(12) United States Patent
Htun et al.

(10) Patent No.: US 8,058,395 B2
(45) Date of Patent: Nov. 15, 2011

(54) CHIMERIC PROTEIN COMPRISING A GREEN FLUORESCENT PTOTEIN FUSED TO A TRANSCRIPTION FACTOR

(75) Inventors: Han Htun, Los Angeles, CA (US); Gordon L. Hager, Garrett Park, MD (US)

(73) Assignees: Han Htun, Los Angeles, CA (US); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 12/004,694

(22) Filed: Dec. 20, 2007

(65) Prior Publication Data
US 2009/0181372 A1 Jul. 16, 2009

Related U.S. Application Data

(62) Division of application No. 10/001,486, filed on Nov. 15, 2001, now Pat. No. 7,312,032, which is a division of application No. 09/091,042, filed as application No. PCT/US96/19516 on Dec. 6, 1996, now Pat. No. 6,455,300.

(60) Provisional application No. 60/008,373, filed on Dec. 8, 1995.

(51) Int. Cl.
C07K 14/00 (2006.01)
C07K 1/00 (2006.01)

(52) U.S. Cl. ......................................... 530/350; 530/402

(58) Field of Classification Search .......................... None
See application file for complete search history.

(56) References Cited

U.S. PATENT DOCUMENTS
2003/0077645 A1* 4/2003 Hager et al. ........................ 435/6

FOREIGN PATENT DOCUMENTS
WO WO/9507463 3/1995
WO WO/9521191 8/1995

OTHER PUBLICATIONS

Ogawa, et al., 1995 *Proc. Natl. Acad. Sci.* "Localization, trafficking, and temperature-dependence of the *Aequorea* green fluorescent protein in cultured vertebrate cells," 92:11899-11903 (Exhibit 3).
Macara, et al., 1995 *Mole. Bio. Of the Cell* "Real-time detection of ligand-induced nuclear transport using a Glucocorticoid Receptor-Green Fluorescent Protein Fusion Construct," 313A (Exhibit 4).
Htun, et al., 1995 *Molecular Bio. Of the Cell* "GFP-GR: A Model System for Studying Cytoplasm-To-Nuclear Translocation and Nuclear Architecture in Cultured Living Cells," 232A. (Exhibit 5).
Helm, et al., 1995 *Nature* "Anticipated stimuli across skin," 373:663-664. (Exhibit 6).
Prasher, et al., 1995 TIG "Using GFP to see the light," 11:320-323. (Exhibit 7).
Cubitt et al., 1995 *TIBS* "Understanding, improving and using green fluorescent proteins," 20:448-455. (Exhibit 8).
Chakraborti et al., 1991 *Journ. of Bio. Chem.* "Creation of "Super" Glucocorticoid Receptors by Point Mutations in the Steroid Binding Domain," 266:22075-22078. (Exhibit 9).
Wang, et al., 1994 *Nature* "Implications for *bcd* mRNA localization from spatial distribution of *exu* protein in *Dropsohila* oogenesis," 369:400-403. (Exhibit 10).
Chalfie, et al., 1994 *Science* "Green Fluorescent Protein as a Marker for Gene Expression,"263:802-805. (Exhibit 11).
Htun, et al., 1996 *Proc. Natl. Acad.* "Visualization of glucocorticoid receptor translocation and intranuclear organization in living cells with a green fluorescent protein chimera," 93:4845-4850. (Exhibit 12).
Carey, et al., 1996 *J. Cell Bio.* "Evidence Using a Green Fluorescent Protein-Glucocorticoid Receptor Chimera that the RAN/TC4 GTPase Mediates an Essential Function Independent of Nuclear Protein Import," 133:985-996. (Exhibit 13).
Heim, R et al., (1995) "Improved green fluorescence", *Nature* 373:663-4.—Exhibit 14.
Kaether, C et al., (1995) "Visualization of protein transport along the secretory pathways using green fluorescent protein", *FEBS Lett*, 369:267-71.—Exhibit 15.
Lim, CR et al., (1995) "Thermosensitivity of green fluorescent protein fluorescence utilized to reveal novel nuclear-like compartments in a mutant nucleoporin NSP1", *J. Biochem* 118:13-7.—Exhibit 16.
Rizzuto R, et al. (1996) "Double labelling of subcellular structures with organelle-targeted GFP mutants in vivo," *Curr Biol*, 6:183-8—Exhibit 17.
Robinett, CC et al., (1996) "In vivo localization of DNA sequences and visualization of large-scale chromatin organization using lac operator/repressor recognition", *J Cell Biol*, 135:1685-700—Exhibit 18. Straight, AF et al. (1996) GFP tagging of budding yeast chromosomes reveals that protein-protein interactions can mediate sister chromatid cohesion, *Curr Biol*, 6:1599-608—Exhibit 19.

* cited by examiner

*Primary Examiner* — Bradley L Sisson
(74) *Attorney, Agent, or Firm* — Adriano & Associates

(57) ABSTRACT

The present invention provides a method of screening for a compound that binds to a selected nucleic acid comprising contacting compound fluorescently labeled by a fluorescent protein with a cell having a plurality of copies of the nucleic acid in an array such that the nucleic acid can be directly detected when bound by fluorescently labeled compound; and directly detecting the location of fluorescence within the cell, fluorescence aggregated at the site of the nucleic acid array indicating a compound that binds to the selected nucleic acid. In particular compounds such a transcription factors can be screened. Reagents for such method are provided including a mammalian cell having a plurality of steroid receptor response elements in an array such that the response element can be directly detected when bound by fluorescently labeled steroid receptor and a chimeric protein comprising a fluorescent protein fused to a steroid receptor.

8 Claims, 6 Drawing Sheets

Confocal Sections

3134 Nucleus

GFP-GR Localization
in MCF7 Cells

Dex

GFP-GR Localization
in MCF7 Cells

RU486

Nuclear Localization
of GFP-ER

MCF7

Nuclear Localization
of GFP-ER

MDA-MB-231

SEQUENCE LISTING

```
<160> NUMBER OF SEQ ID NOS: 9

<210> SEQ ID NO 1
<211> LENGTH: 7257
<212> TYPE: DNA
<213> ORGANISM: Aequorea victoria
<220> FEATURE:
<221> NAME/KEY: CDS
<222> LOCATION: (1072)..(4284)

<400> SEQUENCE: 1
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat     300
agtaacgcca tagggactt tccattgacg tcaatgggtg gagtatttac ggtaaactgc     360
ccacttggca gtacatcaag tgtatcatat gccaagtccg cccctattg acgtcaatga     420 cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca agtctccacc ccattgacgt     600
caatgggagt ttgttttggc accaaaatca acgggacttt ccaaaatgtc gtaataaccc     660
cgccccgttg acgcaaatgg gcggtaggcg tgtacggtgg gaggtctata taagcagagc     720
tcgtttagtg aaccgtcaga tcactagaag ctttattgcg gtagtttatc acagttaaat     780
tgctaacgca gtcagtgctt ctgacacaac agtctcgaac ttaagctgca gaagttggtc     840
gtgaggcact gggcaggtaa gtatcaaggt tacaagacag gtttaaggag accaatagaa     900
actgggcttg tcgagacaga gaagactctt gcgtttctga taggcaccta ttggtcttac     960
tgacatccac tttgcctttc tctccacagg tgtccactcc cagttcaatt acagctctta    1020
aggctagagt acttaatacg actcactata ggctagcgaa ggagatccgc c atg gcc    1077
                                                            Met Ala
                                                              1 cac cat cac cac cat cac gga tat cca tac gac gtg cca gat tac gct    1125
His His His His His His Gly Tyr Pro Tyr Asp Val Pro Asp Tyr Ala
```

```
                5                      10                     15
cag tcg agt gcc atg agt aaa gga gaa gaa ctt ttc act gga gtt gtc    1173
Gln Ser Ser Ala Met Ser Lys Gly Glu Glu Leu Phe Thr Gly Val Val
         20                  25                  30 cca att ctt gtt gaa tta gat ggt gat gtt aat ggg cac aaa ttt tct    1221
Pro Ile Leu Val Glu Leu Asp Gly Asp Val Asn Gly His Lys Phe Ser
 35                  40                  45                  50 gtc agt gga gag ggt gaa ggt gat gca aca tac gga aaa ctt acc ctt    1269
Val Ser Gly Glu Gly Glu Gly Asp Ala Thr Tyr Gly Lys Leu Thr Leu
                 55                  60                  65 aaa ttt att tgc act act gga aaa cta cct gtt cct tgg cca aca ctt    1317
Lys Phe Ile Cys Thr Thr Gly Lys Leu Pro Val Pro Trp Pro Thr Leu
             70                  75                  80 gtc act act ttc act tat ggt gtt caa tgc ttt tca aga tac cca gat    1365
Val Thr Thr Phe Thr Tyr Gly Val Gln Cys Phe Ser Arg Tyr Pro Asp
                 85                  90                  95 cat atg aaa cag cat gac ttt ttc aag agt gcc atg ccc gaa ggt tat    1413
His Met Lys Gln His Asp Phe Phe Lys Ser Ala Met Pro Glu Gly Tyr
100                 105                 110 gta cag gaa aga act ata ttt ttc aaa gat gac ggg aac tac aag aca    1461
Val Gln Glu Arg Thr Ile Phe Phe Lys Asp Asp Gly Asn Tyr Lys Thr
115                 120                 125                 130 cgt gct gaa gtc aag ttt gaa ggt gat acc ctt gtt aat aga atc gag    1509
Arg Ala Glu Val Lys Phe Glu Gly Asp Thr Leu Val Asn Arg Ile Glu
                135                 140                 145 tta aaa ggt att gat ttt aaa gaa gat gga aac att ctt gga cac aaa    1557
Leu Lys Gly Ile Asp Phe Lys Glu Asp Gly Asn Ile Leu Gly His Lys
            150                 155                 160 ttg gaa tac aac tat aac tca cac aat gta tac atc atg gca gac aaa    1605
Leu Glu Tyr Asn Tyr Asn Ser His Asn Val Tyr Ile Met Ala Asp Lys
            165                 170                 175 caa aag aat gga atc aaa gtt aac ttc aaa att aga cac aac att gaa    1653
Gln Lys Asn Gly Ile Lys Val Asn Phe Lys Ile Arg His Asn Ile Glu
180                 185                 190 gat gga agc gtt caa cta gca gac cat tat caa caa aat act cca att    1701
Asp Gly Ser Val Gln Leu Ala Asp His Tyr Gln Gln Asn Thr Pro Ile
195                 200                 205                 210 ggc gat ggc cct gtc ctt tta cca gac aac cat tac ctg tcc aca caa    1749
Gly Asp Gly Pro Val Leu Leu Pro Asp Asn His Tyr Leu Ser Thr Gln
                215                 220                 225 tct gcc ctt tcg aaa gat ccc aac gaa aag aga gac cac atg gtc ctt    1797
Ser Ala Leu Ser Lys Asp Pro Asn Glu Lys Arg Asp His Met Val Leu
            230                 235                 240 ctt gag ttt gta aca gct gct ggg att aca cat ggc atg gat gaa cta    1845
Leu Glu Phe Val Thr Ala Ala Gly Ile Thr His Gly Met Asp Glu Leu
            245                 250                 255 tac aaa ggc gcc ggc gct ggt gct ggt gct ggc gcc atc agc gcg ctg    1893
Tyr Lys Gly Ala Gly Ala Gly Ala Gly Ala Gly Ala Ile Ser Ala Leu
260                 265                 270 atc ctg gac tcc aaa gaa tcc tta gct ccc cct ggt aga gac gaa gtc    1941
Ile Leu Asp Ser Lys Glu Ser Leu Ala Pro Pro Gly Arg Asp Glu Val
275                 280                 285                 290 cct ggc agt ttg ctt ggc cag ggg agg ggg agc gta atg gac ttt tat    1989
Pro Gly Ser Leu Leu Gly Gln Gly Arg Gly Ser Val Met Asp Phe Tyr
                295                 300                 305 aaa agc ctg agg gga gga gct aca gtc aag gtt tct gca tct tcg ccc    2037
Lys Ser Leu Arg Gly Gly Ala Thr Val Lys Val Ser Ala Ser Ser Pro
            310                 315                 320 tca gtg gct gct gct tct cag gca gat tcc aag cag cag agg att ctc    2085
Ser Val Ala Ala Ala Ser Gln Ala Asp Ser Lys Gln Gln Arg Ile Leu
```

```
                   325                 330                 335
ctt  gat  ttc  tcg  aaa  ggc  tcc  aca  agc  aat  gtg  cag  cag  cga  cag  cag        2133
Leu  Asp  Phe  Ser  Lys  Gly  Ser  Thr  Ser  Asn  Val  Gln  Gln  Arg  Gln  Gln
     340                 345                 350 cag  cag  cag  cag  cag  cag  cag  cag  cag  cag  cag  cag  cag  cag  cag  cag        2181
Gln  Gln  Gln  Gln  Gln  Gln  Gln  Gln  Gln  Gln  Gln  Gln  Gln  Gln  Gln  Gln
355                 360                 365                 370 cag  cca  ggc  tta  tcc  aaa  gcc  gtt  tca  ctg  tcc  atg  ggg  ctg  tat  atg        2229
Gln  Pro  Gly  Leu  Ser  Lys  Ala  Val  Ser  Leu  Ser  Met  Gly  Leu  Tyr  Met
               375                 380                 385 gga  gag  aca  gaa  aca  aaa  gtg  atg  ggg  aat  gac  ttg  ggc  tac  cca  cag        2277
Gly  Glu  Thr  Glu  Thr  Lys  Val  Met  Gly  Asn  Asp  Leu  Gly  Tyr  Pro  Gln
     390                 395                 400 cag  ggc  caa  ctt  ggc  ctt  tcc  tct  ggg  gaa  aca  gac  ttt  cgg  ctt  ctg        2325
Gln  Gly  Gln  Leu  Gly  Leu  Ser  Ser  Gly  Glu  Thr  Asp  Phe  Arg  Leu  Leu
405                 410                 415 gaa  gaa  agc  att  gca  aac  ctc  aat  agg  tcg  acc  agc  gtt  cca  gag  aac        2373
Glu  Glu  Ser  Ile  Ala  Asn  Leu  Asn  Arg  Ser  Thr  Ser  Val  Pro  Glu  Asn
               420                 425                 430 ccc  aag  agt  tca  acg  tct  gca  act  ggg  tgt  gct  acc  ccg  aca  gag  aag        2421
Pro  Lys  Ser  Ser  Thr  Ser  Ala  Thr  Gly  Cys  Ala  Thr  Pro  Thr  Glu  Lys
435                 440                 445                 450 gag  ttt  ccc  aaa  act  cac  tcg  gat  gca  tct  tca  gaa  cag  caa  aat  cga        2469
Glu  Phe  Pro  Lys  Thr  His  Ser  Asp  Ala  Ser  Ser  Glu  Gln  Gln  Asn  Arg
                    455                 460                 465 aaa  agc  cag  acc  ggc  acc  aac  gga  ggc  agt  gtg  aaa  ttg  tat  ccc  aca        2517
Lys  Ser  Gln  Thr  Gly  Thr  Asn  Gly  Gly  Ser  Val  Lys  Leu  Tyr  Pro  Thr
               470                 475                 480 gac  caa  agc  acc  ttt  gac  ctc  ttg  aag  gat  ttg  gag  ttt  tcc  gct  ggg        2565
Asp  Gln  Ser  Thr  Phe  Asp  Leu  Leu  Lys  Asp  Leu  Glu  Phe  Ser  Ala  Gly
          485                 490                 495 tcc  cca  agt  aaa  gac  aca  aac  gag  agt  ccc  tgg  aga  tca  gat  ctg  ttg        2613
Ser  Pro  Ser  Lys  Asp  Thr  Asn  Glu  Ser  Pro  Trp  Arg  Ser  Asp  Leu  Leu
500                 505                 510 ata  gat  gaa  aac  ttg  ctt  tct  cct  ttg  gcg  gga  gaa  gat  gat  cca  ttc        2661
Ile  Asp  Glu  Asn  Leu  Leu  Ser  Pro  Leu  Ala  Gly  Glu  Asp  Asp  Pro  Phe
515                 520                 525                 530 ctt  ctc  gaa  ggg  aac  acg  aat  gag  gat  tgt  aag  cct  ctt  att  tta  ccg        2709
Leu  Leu  Glu  Gly  Asn  Thr  Asn  Glu  Asp  Cys  Lys  Pro  Leu  Ile  Leu  Pro
               535                 540                 545 gac  act  aaa  cct  aaa  att  aag  gat  act  gga  gat  aca  atc  tta  tca  agt        2757
Asp  Thr  Lys  Pro  Lys  Ile  Lys  Asp  Thr  Gly  Asp  Thr  Ile  Leu  Ser  Ser
               550                 555                 560 ccc  agc  agt  gtg  gca  cta  ccc  caa  gtg  aaa  aca  gaa  aaa  gat  gat  ttc        2805
Pro  Ser  Ser  Val  Ala  Leu  Pro  Gln  Val  Lys  Thr  Glu  Lys  Asp  Asp  Phe
          565                 570                 575 att  gaa  ctt  tgc  acc  ccc  ggg  gta  att  aag  caa  gag  aaa  ctg  ggc  cca        2853
Ile  Glu  Leu  Cys  Thr  Pro  Gly  Val  Ile  Lys  Gln  Glu  Lys  Leu  Gly  Pro
580                 585                 590 gtt  tat  tgt  cag  gca  agc  ttt  tct  ggg  aca  aat  ata  att  ggt  aat  aaa        2901
Val  Tyr  Cys  Gln  Ala  Ser  Phe  Ser  Gly  Thr  Asn  Ile  Ile  Gly  Asn  Lys
595                 600                 605                 610 atg  tct  gcc  att  tct  gtt  cat  ggt  gtg  agt  acc  tct  gga  gga  cag  atg        2949
Met  Ser  Ala  Ile  Ser  Val  His  Gly  Val  Ser  Thr  Ser  Gly  Gly  Gln  Met
               615                 620                 625 tac  cac  tat  gac  atg  aat  aca  gca  tcc  ctt  tct  cag  cag  cag  gat  cag        2997
Tyr  His  Tyr  Asp  Met  Asn  Thr  Ala  Ser  Leu  Ser  Gln  Gln  Gln  Asp  Gln
          630                 635                 640 aag  cct  gtt  ttt  aat  gtc  att  cca  cca  att  cct  gtt  ggt  tct  gaa  aac        3045
Lys  Pro  Val  Phe  Asn  Val  Ile  Pro  Pro  Ile  Pro  Val  Gly  Ser  Glu  Asn
```

```
                      645                 650                 655
tgg aat agg tgc caa ggc tcc gga gag gac agc ctg act tcc ttg ggg    3093
Trp Asn Arg Cys Gln Gly Ser Gly Glu Asp Ser Leu Thr Ser Leu Gly
660                 665                 670 gct ctg aac ttc cca ggc cgg tca gtg ttt tct aat ggg tac tca agc    3141
Ala Leu Asn Phe Pro Gly Arg Ser Val Phe Ser Asn Gly Tyr Ser Ser
675                 680                 685                 690 cct gga atg aga cca gat gta agc tct cct cca tcc agc tcg tca gca    3189
Pro Gly Met Arg Pro Asp Val Ser Ser Pro Pro Ser Ser Ser Ser Ala
            695                 700                 705 gcc acg gga cca cct ccc aag ctc tgc ctg gtg tgc tcc gat gaa gct    3237
Ala Thr Gly Pro Pro Pro Lys Leu Cys Leu Val Cys Ser Asp Glu Ala
        710                 715                 720 tca gga tgt cat tac ggg gtg ctg aca tgt gga agc tgc aaa gta ttc    3285
Ser Gly Cys His Tyr Gly Val Leu Thr Cys Gly Ser Cys Lys Val Phe
    725                 730                 735 ttt aaa aga gca gtg gaa gga cag cac aat tac ctt tgt gct gga aga    3333
Phe Lys Arg Ala Val Glu Gly Gln His Asn Tyr Leu Cys Ala Gly Arg
740                 745                 750 aac gat tgc atc att gat aaa att cga agg aaa aac tgc cca gca tgc    3381
Asn Asp Cys Ile Ile Asp Lys Ile Arg Arg Lys Asn Cys Pro Ala Cys
755                 760                 765                 770 cgc tat cgg aaa tgt ctt cag gct gga atg aac ctt gaa gct cga aaa    3429
Arg Tyr Arg Lys Cys Leu Gln Ala Gly Met Asn Leu Glu Ala Arg Lys
            775                 780                 785 aca aag aaa aaa atc aaa ggg att cag caa gcc act gca gga gtc tca    3477
Thr Lys Lys Lys Ile Lys Gly Ile Gln Gln Ala Thr Ala Gly Val Ser
        790                 795                 800 caa gac act tcg gaa aat cct aac aaa aca ata gtt cct gca gca tta    3525
Gln Asp Thr Ser Glu Asn Pro Asn Lys Thr Ile Val Pro Ala Ala Leu
    805                 810                 815 cca cag ctc acc cct acc ttg gtg tca ctg ctg gag gtg att gaa ccc    3573
Pro Gln Leu Thr Pro Thr Leu Val Ser Leu Leu Glu Val Ile Glu Pro
820                 825                 830 gag gtg ttg tat gca gga tat gat agc tct gtt cca gat tca gca tgg    3621
Glu Val Leu Tyr Ala Gly Tyr Asp Ser Ser Val Pro Asp Ser Ala Trp
835                 840                 845                 850 aga att atg acc aca ctc aac atg tta ggt ggg cgt caa gtg att gca    3669
Arg Ile Met Thr Thr Leu Asn Met Leu Gly Gly Arg Gln Val Ile Ala
            855                 860                 865 gca gtg aaa tgg gca aag gcg ata cta ggc ttg aga aac tta cac ctc    3717
Ala Val Lys Trp Ala Lys Ala Ile Leu Gly Leu Arg Asn Leu His Leu
        870                 875                 880 gat gac caa atg acc ctg cta cag tac tca tgg atg ttt ctc atg gca    3765
Asp Asp Gln Met Thr Leu Leu Gln Tyr Ser Trp Met Phe Leu Met Ala
    885                 890                 895 ttt gcc ttg ggt tgg aga tca tac aga caa tca agc gga aac ctg ctc    3813
Phe Ala Leu Gly Trp Arg Ser Tyr Arg Gln Ser Ser Gly Asn Leu Leu
900                 905                 910 tgc ttt gct cct gat ctg att att aat gag cag aga atg tct cta ccc    3861
Cys Phe Ala Pro Asp Leu Ile Ile Asn Glu Gln Arg Met Ser Leu Pro
915                 920                 925                 930 ggc atg tat gac caa tgt aaa cac atg ctg ttt gtc tcc tct gaa tta    3909
Gly Met Tyr Asp Gln Cys Lys His Met Leu Phe Val Ser Ser Glu Leu
            935                 940                 945 caa aga ttg cag gta tcc tat gaa gag tat ctc tgt atg aaa acc tta    3957
Gln Arg Leu Gln Val Ser Tyr Glu Glu Tyr Leu Cys Met Lys Thr Leu
        950                 955                 960 ctg ctt ctc tcc tca gtt cct aag gaa ggt ctg aag agc caa gag tta    4005
Leu Leu Leu Ser Ser Val Pro Lys Glu Gly Leu Lys Ser Gln Glu Leu
```

-continued

```
              965                 970                 975
ttt gat gag att cga atg act tat atc aaa gag cta gga aaa gcc atc         4053
Phe Asp Glu Ile Arg Met Thr Tyr Ile Lys Glu Leu Gly Lys Ala Ile
    980                 985                 990 gtc aaa agg gaa ggg aac tcc agt cag aac tgg caa cgg ttt tac             4098
Val Lys Arg Glu Gly Asn Ser Ser Gln Asn Trp Gln Arg Phe Tyr
995                 1000                1005 caa ctg aca aag ctt ctg gac tcc atg cat gag gtg gtt gag aat             4143
Gln Leu Thr Lys Leu Leu Asp Ser Met His Glu Val Val Glu Asn
1010                1015                1020 ctc ctt acc tac tgc ttc cag aca ttt ttg gat aag acc atg agt             4188
Leu Leu Thr Tyr Cys Phe Gln Thr Phe Leu Asp Lys Thr Met Ser
1025                1030                1035 att gaa ttc cca gag atg tta gct gaa atc atc act aat cag ata             4233
Ile Glu Phe Pro Glu Met Leu Ala Glu Ile Ile Thr Asn Gln Ile
1040                1045                1050 cca aaa tat tca aat gga aat atc aaa aag ctt ctg ttt cat caa             4278
Pro Lys Tyr Ser Asn Gly Asn Ile Lys Lys Leu Leu Phe His Gln
1055                1060                1065 aaa tga ctgccttact aagaaaggtt gccttaaaga agttgaatt tatagtctag           4334
Lys
1070 agtcgacccg gcggccgct tcgagcagac atgataagat acattgatga gtttggacaa        4394
accacaacta gaatgcagtg aaaaaaatgc tttatttgtg aaatttgtga tgctattgct       4454
ttatttgtaa ccattataag ctgcaataaa caagttaaca acaacaattg cattcatttt       4514
atgtttcagg ttcaggggga gatgtgggag gtttttttaaa gcaagtaaaa cctctacaaa      4574
tgtggtaaaa tcgataagga tccgggctgg cgtaatagcg aagaggcccg caccgatcgc       4634
ccttcccaac agttgcgcag cctgaatggc gaatggacgc gccctgtagc ggcgcattaa       4694
gcgcggcggg tgtggtggtt acgcgcagcg tgaccgctac acttgccagc gccctagcgc       4754
ccgctccttt cgctttcttc ccttcctttc tcgccacgtt cgccggcttt ccccgtcaag       4814
ctctaaatcg gggctccct ttagggttcc gatttagagc tttacggcac ctcgaccgca       4874
aaaaacttga tttgggtgat ggttcacgta gtgggccatc gccctgatag acggtttttc      4934
gccctttgac gttggagtcc acgttcttta atagtggact cttgttccaa actggaacaa      4994
cactcaaccc tatctcggtc tattcttttg atttataagg gattttgccg atttcggcct     5054
attggttaaa aaatgagctg atttaacaaa tatttaacgc gaattttaac aaaatattaa     5114
cgtttacaat ttcgcctgat gcggtatttt ctccttacgc atctgtgcgg tatttcacac     5174
cgcatatggt gcactctcag tacaatctgc tctgatgccg catagttaag ccagccccga     5234
cacccgccaa cacccgctga cgcgccctga cgggcttgtc tgctcccggc atccgcttac     5294
agacaagctg tgaccgtctc cgggagctgc atgtgtcaga ggttttcacc gtcatcaccg     5354
aaacgcgcga cgaaagggg cctcgtgata cgcctatttt tataggttaa tgtcatgata     5414
ataatggttt cttagacgtc aggtggcact tttcgggaa atgtgcgcgg aaccccctatt    5474
tgtttattttt tctaaataca ttcaaatatg tatccgctca tgagacaata accctgataa    5534
atgcttcaat aatattgaaa aaggaagagt atgagtattc aacatttccg tgtcgccctt    5594
attccctttt tgcggcatt ttgccttcct gttttgctc acccagaaac gctggtgaaa      5654
gtaaaagatg ctgaagatca gttgggtgca cgagtgggtt acatcgaact ggatctcaac    5714
agcggtaaga tccttgagag ttttcgcccc gaagaacgtt ttccaatgat gagcactttt    5774
aaagttctgc tatgtggcgc ggtattatcc cgtattgacg ccgggcaaga gcaactcggt    5834
```

```
cgccgcatac actattctca gaatgacttg gttgagtact caccagtcac agaaaagcat    5894
cttacggatg gcatgacagt aagagaatta tgcagtgctg ccataaccat gagtgataac    5954
actgcggcca acttacttct gacaacgatc ggaggaccga aggagctaac cgctttttg     6014 cacaacatgg gggatcatgt aactcgcctt gatcgttggg aaccggagct gaatgaagcc    6074
ataccaaacg acgagcgtga caccacgatg cctgtagcaa tggcaacaac gttgcgcaaa    6134
ctattaactg gcgaactact tactctagct tcccggcaac aattaataga ctggatggag    6194
gcggataaag ttgcaggacc acttctgcgc tcggcccttc cggctggctg gtttattgct    6254
gataaatctg gagccggtga gcgtgggtct cgcggtatca ttgcagcact ggggccagat    6314
ggtaagccct cccgtatcgt agttatctac acgacgggga gtcaggcaac tatggatgaa    6374
cgaaatagac agatcgctga gataggtgcc tcactgatta gcattggta  actgtcagac    6434 caagtttact catatatact ttagattgat ttaaaacttc atttttaatt taaaaggatc    6494
taggtgaaga tccttttga  taatctcatg accaaaatcc cttaacgtga gttttcgttc    6554
cactgagcgt cagaccccgt agaaaagatc aaaggatctt cttgagatcc ttttttctg     6614 cgcgtaatct gctgcttgca acaaaaaaa ccaccgctac cagcggtggt ttgtttgccg     6674
gatcaagagc taccaactct ttttccgaag gtaactggct tcagcagagc gcagatacca    6734
aatactgtcc ttctagtgta gccgtagtta ggccaccact tcaagaactc tgtagcaccg    6794
cctacatacc tcgctctgct aatcctgtta ccagtggctg ctgccagtgg cgataagtcg    6854
tgtcttaccg ggttggactc aagacgatag ttaccggata aggcgcagcg gtcgggctga    6914
acggggggtt cgtgcacaca gcccagcttg gagcgaacga cctacaccga actgagatac    6974
ctacagcgtg agctatgaga aagcgccacg cttcccgaag ggagaaaggc ggacaggtat    7034
ccggtaagcg gcagggtcgg aacaggagag cgcacgaggg agcttccagg gggaaacgcc    7094
tggtatcttt atagtcctgt cgggtttcgc cacctctgac ttgagcgtcg attttgtga    7154 tgctcgtcag gggggcggag cctatggaaa aacgccagca acgcggcctt tttacggttc    7214
ctggcctttt gctggccttt tgctcacatg gctcgacaga tct                      7257
```

<210> SEQ ID NO 2
<211> LENGTH: 1070
<212> TYPE: PRT
<213> ORGANISM: Aequorea victoria

<400> SEQUENCE: 2

```
Met Ala His His His His His His Gly Tyr Pro Tyr Asp Val Pro Asp
1               5                   10                  15

Tyr Ala Gln Ser Ser Ala Met Ser Lys Gly Glu Glu Leu Phe Thr Gly
            20                  25                  30

Val Val Pro Ile Leu Val Glu Leu Asp Gly Asp Val Asn Gly His Lys
        35                  40                  45

Phe Ser Val Ser Gly Glu Gly Glu Gly Asp Ala Thr Tyr Gly Lys Leu
    50                  55                  60

Thr Leu Lys Phe Ile Cys Thr Thr Gly Lys Leu Pro Val Pro Trp Pro
65                  70                  75                  80

Thr Leu Val Thr Thr Phe Thr Tyr Gly Val Gln Cys Phe Ser Arg Tyr
                85                  90                  95

Pro Asp His Met Lys Gln His Asp Phe Phe Lys Ser Ala Met Pro Glu
            100                 105                 110

Gly Tyr Val Gln Glu Arg Thr Ile Phe Phe Lys Asp Asp Gly Asn Tyr
        115                 120                 125
```

-continued

```
Lys Thr Arg Ala Glu Val Lys Phe Glu Gly Asp Thr Leu Val Asn Arg
    130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
            180                 185                 190

Ile Glu Asp Gly Ser Val Gln Leu Ala Asp His Tyr Gln Gln Asn Thr
        195                 200                 205

Pro Ile Gly Asp Gly Pro Val Leu Leu Pro Asp Asn His Tyr Leu Ser
    210                 215                 220

Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr His Gly Met Asp
                245                 250                 255

Glu Leu Tyr Lys Gly Ala Gly Ala Gly Ala Gly Ala Ile Ser
            260                 265                 270

Ala Leu Ile Leu Asp Ser Lys Glu Ser Leu Ala Pro Pro Gly Arg Asp
        275                 280                 285

Glu Val Pro Gly Ser Leu Leu Gly Gln Gly Arg Gly Ser Val Met Asp
    290                 295                 300

Phe Tyr Lys Ser Leu Arg Gly Gly Ala Thr Val Lys Val Ser Ala Ser
305                 310                 315                 320

Ser Pro Ser Val Ala Ala Ala Ser Gln Ala Asp Ser Lys Gln Gln Arg
                325                 330                 335

Ile Leu Leu Asp Phe Ser Lys Gly Ser Thr Ser Asn Val Gln Gln Arg
            340                 345                 350

Gln Gln Gln Gln Gln Gln Gln Gln Gln Gln Gln Gln Gln Gln Gln
        355                 360                 365

Gln Gln Gln Pro Gly Leu Ser Lys Ala Val Ser Leu Ser Met Gly Leu
    370                 375                 380

Tyr Met Gly Glu Thr Glu Thr Lys Val Met Gly Asn Asp Leu Gly Tyr
385                 390                 395                 400

Pro Gln Gln Gly Gln Leu Gly Leu Ser Ser Gly Glu Thr Asp Phe Arg
                405                 410                 415

Leu Leu Glu Glu Ser Ile Ala Asn Leu Asn Arg Ser Thr Ser Val Pro
            420                 425                 430

Glu Asn Pro Lys Ser Ser Thr Ser Ala Thr Gly Cys Ala Thr Pro Thr
        435                 440                 445

Glu Lys Glu Phe Pro Lys Thr His Ser Asp Ala Ser Ser Glu Gln Gln
    450                 455                 460

Asn Arg Lys Ser Gln Thr Gly Thr Asn Gly Gly Ser Val Lys Leu Tyr
465                 470                 475                 480

Pro Thr Asp Gln Ser Thr Phe Asp Leu Leu Lys Asp Leu Glu Phe Ser
                485                 490                 495

Ala Gly Ser Pro Ser Lys Asp Thr Asn Glu Ser Pro Trp Arg Ser Asp
            500                 505                 510

Leu Leu Ile Asp Glu Asn Leu Leu Ser Pro Leu Ala Gly Glu Asp Asp
        515                 520                 525

Pro Phe Leu Leu Glu Gly Asn Thr Asn Glu Asp Cys Lys Pro Leu Ile
    530                 535                 540

Leu Pro Asp Thr Lys Pro Lys Ile Lys Asp Thr Gly Asp Thr Ile Leu
545                 550                 555                 560
```

```
Ser Ser Pro Ser Ser Val Ala Leu Pro Gln Val Lys Thr Glu Lys Asp
            565                 570                 575

Asp Phe Ile Glu Leu Cys Thr Pro Gly Val Ile Lys Gln Glu Lys Leu
            580                 585                 590

Gly Pro Val Tyr Cys Gln Ala Ser Phe Ser Gly Thr Asn Ile Ile Gly
            595                 600                 605

Asn Lys Met Ser Ala Ile Ser Val His Gly Val Ser Thr Ser Gly Gly
            610                 615                 620

Gln Met Tyr His Tyr Asp Met Asn Thr Ala Ser Leu Ser Gln Gln Gln
625                 630                 635                 640

Asp Gln Lys Pro Val Phe Asn Val Ile Pro Ile Pro Val Gly Ser
            645                 650                 655

Glu Asn Trp Asn Arg Cys Gln Gly Ser Gly Glu Asp Ser Leu Thr Ser
            660                 665                 670

Leu Gly Ala Leu Asn Phe Pro Gly Arg Ser Val Phe Ser Asn Gly Tyr
            675                 680                 685

Ser Ser Pro Gly Met Arg Pro Asp Val Ser Ser Pro Pro Ser Ser Ser
            690                 695                 700

Ser Ala Ala Thr Gly Pro Pro Lys Leu Cys Leu Val Cys Ser Asp
705                 710                 715                 720

Glu Ala Ser Gly Cys His Tyr Gly Val Leu Thr Cys Gly Ser Cys Lys
            725                 730                 735

Val Phe Phe Lys Arg Ala Val Glu Gly Gln His Asn Tyr Leu Cys Ala
            740                 745                 750

Gly Arg Asn Asp Cys Ile Ile Asp Lys Ile Arg Arg Lys Asn Cys Pro
            755                 760                 765

Ala Cys Arg Tyr Arg Lys Cys Leu Gln Ala Gly Met Asn Leu Glu Ala
            770                 775                 780

Arg Lys Thr Lys Lys Lys Ile Lys Gly Ile Gln Gln Ala Thr Ala Gly
785                 790                 795                 800

Val Ser Gln Asp Thr Ser Glu Asn Pro Asn Lys Thr Ile Val Pro Ala
            805                 810                 815

Ala Leu Pro Gln Leu Thr Pro Thr Leu Val Ser Leu Leu Glu Val Ile
            820                 825                 830

Glu Pro Glu Val Leu Tyr Ala Gly Tyr Asp Ser Ser Val Pro Asp Ser
            835                 840                 845

Ala Trp Arg Ile Met Thr Thr Leu Asn Met Leu Gly Gly Arg Gln Val
850                 855                 860

Ile Ala Ala Val Lys Trp Ala Lys Ala Ile Leu Gly Leu Arg Asn Leu
865                 870                 875                 880

His Leu Asp Asp Gln Met Thr Leu Leu Gln Tyr Ser Trp Met Phe Leu
            885                 890                 895

Met Ala Phe Ala Leu Gly Trp Arg Ser Tyr Arg Gln Ser Ser Gly Asn
            900                 905                 910

Leu Leu Cys Phe Ala Pro Asp Leu Ile Ile Asn Glu Gln Arg Met Ser
            915                 920                 925

Leu Pro Gly Met Tyr Asp Gln Cys Lys His Met Leu Phe Val Ser Ser
            930                 935                 940

Glu Leu Gln Arg Leu Gln Val Ser Tyr Glu Glu Tyr Leu Cys Met Lys
945                 950                 955                 960

Thr Leu Leu Leu Leu Ser Ser Val Pro Lys Glu Gly Leu Lys Ser Gln
            965                 970                 975

Glu Leu Phe Asp Glu Ile Arg Met Thr Tyr Ile Lys Glu Leu Gly Lys
```

| | | | |
|---|---|---|---|
| | 980 | 985 | 990 |

Ala Ile Val Lys Arg Glu Gly Asn  Ser Ser Gln Asn Trp  Gln Arg Phe
                       995                     1000                    1005

Tyr Gln  Leu Thr Lys Leu Leu  Asp Ser Met His Glu  Val Val Glu
      1010                  1015                  1020

Asn Leu  Leu Thr Tyr Cys Phe  Gln Thr Phe Leu Asp  Lys Thr Met
      1025                  1030                  1035

Ser Ile  Glu Phe Pro Glu Met  Leu Ala Glu Ile Ile  Thr Asn Gln
      1040                  1045                  1050

Ile Pro  Lys Tyr Ser Asn Gly  Asn Ile Lys Lys Leu  Leu Phe His
      1055                  1060                  1065

Gln Lys
      1070

<210> SEQ ID NO 3
<211> LENGTH: 46
<212> TYPE: DNA
<213> ORGANISM: Artificial
<220> FEATURE:
<223> OTHER INFORMATION: Chemically Synthesized

<400> SEQUENCE: 3
gcgcgctgat cagaattcct tttaggaatt ctgatcagcg cgctga                   46

<210> SEQ ID NO 4
<211> LENGTH: 15
<212> TYPE: DNA
<213> ORGANISM: Homo sapiens
<220> FEATURE:
<221> NAME/KEY: misc_feature
<222> LOCATION: (7)..(9)
<223> OTHER INFORMATION: n is a, c, g, or t

<400> SEQUENCE: 4
agaacannnt gttct                                               15

<210> SEQ ID NO 5
<211> LENGTH: 15
<212> TYPE: DNA
<213> ORGANISM: Homo sapiens
<220> FEATURE:
<221> NAME/KEY: misc_feature
<222> LOCATION: (7)..(9)
<223> OTHER INFORMATION: n is a, c, g, or t

<400> SEQUENCE: 5
aggtcannnt gacct                                               15

<210> SEQ ID NO 6
<211> LENGTH: 60
<212> TYPE: DNA
<213> ORGANISM: Artificial
<220> FEATURE:
<223> OTHER INFORMATION: Chemically Synthesized

<400> SEQUENCE: 6
tcgagcgcgc aagaacacag tgttctgacg acacgaagaa caggatgttc tcgtacagtg     60

<210> SEQ ID NO 7
<211> LENGTH: 60
<212> TYPE: DNA
<213> ORGANISM: Artificial
<220> FEATURE:
<223> OTHER INFORMATION: Chemically Synthesized

```
<400> SEQUENCE: 7
tcgacactgt acgagaacat cctgttcttc gtgtcgtcag aacactgtgt tcttgcgcgc            60

<210> SEQ ID NO 8
<211> LENGTH: 60
<212> TYPE: DNA
<213> ORGANISM: Artificial
<220> FEATURE:
<223> OTHER INFORMATION: Chemically Synthesized

<400> SEQUENCE: 8
tcgagcgcgc aaggtcacag tgacctgacg acacgaaggt caggatgacc tcgtacagtg            60

<210> SEQ ID NO 9
<211> LENGTH: 60
<212> TYPE: DNA
<213> ORGANISM: Artificial
<220> FEATURE:
<223> OTHER INFORMATION: Chemically Synthesized

<400> SEQUENCE: 9
tcgacactgt acgaggtcat cctgaccttc gtgtcgtcag gtcactgtga ccttgcgcgc            60
```

CHIMERIC PROTEIN COMPRISING A GREEN FLUORESCENT PTOTEIN FUSED TO A TRANSCRIPTION FACTOR

The subject application is a divisional of U.S. Ser. No. 10/001,486 filed Nov. 15, 2001 (now U.S. Pat. No. 7,312,032 issued Dec. 25, 2007) which is a divisional of U.S. Ser. No. 09/091,042 filed Feb. 12, 1999 (now U.S. Pat. No. 6,455,300 issued Sep. 24, 2002), which is a National Stage of PCT/US96/19516 with international filing date of Dec. 6, 1996, which claims the priority of U.S. Ser. No. 60/008,373, filed Dec. 8, 1995, which is incorporated herein by reference.

BACKGROUND OF THE INVENTION

1. Field of the Invention

The present invention relates to the field of binding of molecules such as transcription factors to regions of nucleic acids, steroid hormone usage, steroid receptors and their corresponding response elements. Reagents are provided to allow methods involving direct detection of binding of a molecule, determining response element targeting by activated steroid receptors, screening for steroid agonists and antagonists, and monitoring levels of steroid agonists and antagonists in biological samples.

2. Background Art

Steroid receptors are hormone-dependent activators of gene expression. Steroid receptors mediate the action of steroid hormones (e.g., glucocorticoids, estrogens, progestins, testosterone, mineralocorticoids and 1,25-dihydroxycholecalciferol) in human tissues. After activation with the cognate ligand, receptors bind to chromatin in the nucleus and modulate the activity of target cellular genes. The binding of receptors to these target sequences is a key step in steroid function. Currently, this interaction can only be detected by indirect methods, such as reporter assays that detect the result of transcriptional activation coupled with transfection methods that introduce DNA sequences with receptor binding sites.

It is generally accepted that the unliganded glucocorticoid receptor (GR) resides in the cytoplasm, and that hormone activation leads both to nuclear accumulation and gene activation. (Gasc, J.-M. & Baulieu, E. E. (1987) in *Steroid Hormone Receptors: Their Intracellular Localisation*, ed. Clark, C. R. (Ellis Horwood Ltd., Chichester, England), pp. 233-250; Beato, M. (1989) *Cell* 56, 335-344; Carson-Jurica, M. A., Schrader, W. T. & O'Malley, B. W. (1990) *Endocr. Rev.* 11, 201-220; Gronemeyer, H. (1993) in *Steroid Hormone Action*, ed. Parker, M. G. (Oxford University Press, New York), pp. 94-117; Tsai, M. J. & O'Malley, B. W. (1994) *Annu. Rev. Biochem.* 63, 451-486; Akner, G., Wikstrom, A. C. & Gustafsson, J. A. (1995) *J Steroid Biochem. Mol. Biol.* 52, 1-16), and references therein. However, the mechanisms involved in nuclear translocation and targeting of steroid receptors to regulatory sites in chromatin have been poorly understood. It has previously been difficult to discriminate between the ability of a given receptor mutant, or a given receptor/ligand combination, to participate in the separate processes of receptor activation, nuclear translocation, sequence-specific binding, and promoter activation.

Proteins have previously been labeled with fluorescent tags to detect their localization and sometimes their conformational changes both in vitro and in intact cells. Such labeling is essential both for immunofluorescence and for fluorescence analog cytochemistry, in which the biochemistry and trafficking of proteins are monitored after microinjection into living cells (Wang, Y. L. & Taylor, D. L., eds. (1989) *Methods Cell Biol.* 29). Traditionally, fluorescence labeling is done by purifying proteins and then covalently conjugating them to reactive derivatives of organic fluorophores. The stoichiometry and locations of dye attachment are often difficult to control, and careful repurification of the proteins is usually necessary. If the proteins are to be used inside living cells, a final challenging step is to get them across the plasma membrane via micropipet techniques or various methods of reversible permeabilization. Furthermore, in previous hormone studies broken cell preparations or antibody tags in fixed cell preparations were used, both techniques that cause enormous disruption of cell structures.

The green fluorescent protein (GFP) from the jellyfish *Aequorea victoria* is a molecule whose natural function seems to be to convert the blue chemiluminescence of the $Ca^{2+}$-sensitive photoprotein aequorin into green emission (Ward, W. W. (1979) in *Photochemical and Photobiological Reviews*, ed. Smith, K. C. (Plenum, N.Y.), 4:1-57). GFP's absorption bands in the blue (maximally at a wave length of 395 nm with weaker absorbance at 470 nm) and emission peak in the green (at 509 nm) do not arise from a distinct cofactor but rather from an internal p-hydroxybenzylideneimidazolidinone chromophore generated by cyclization and oxidation of a serine-tyrosine-glycine sequence at residues 56-67 (Cody, C. W., Prasher, D. C., Westler, W. M., Prendergast, F. G. & Ward, W. W. (1993) *Biochemistry* 32, 1212-1218). The gene for GFP was cloned (Prasher, D. C., Eckenrode, V. K., Ward, W. W., Prendergast, F. G. & Cormier, M. J. (1992) *Gene* 111, 229-233), and the encoded protein consists of 238 amino acid residues (molecular weight 27 kD). Heterologous expression of the gene has been done in *Escherichia coli* (Heim, R., Prasher, D. C. and Tsien, R. Y. (1994) *Proc. Natl. Acad. Sci. U.S.A.* 91, 12501-12504); Inouye, S. & Tsuji, F. I. (1994) *FEBS Lett.* 341, 277-280), *Caenorhabditis elegans* (Chalfie, M., Tu, Y., Euskirchen, G., Ward, W. W. & Prasher, D. C. (1994) *Science* 263, 802-805), and *Drosophila melanogaster* (Yeh, E., Gustafson, K. & Boulianne, G. L. (1995) *Proc. Natl. Acad. Sci. U.S.A.* 92, 7035-7040; Tannahill, D., Bray, S. & Harris, W. A. (1995) *Dev. Biol.* 168, 694-697 and plants (Hu, W. & Cheng, C. L. (1995) *FEBS Lett.* 369, 331-334; Baulcombe, D. C., Chapman, S. & Santa Cruz, S. (1995) *Plant J.* 7, 1045-1053). Recently, chimeric genes encoding N- and C-terminal fusions of the *Drosophila* exuperantia (exu) gene product, Exu (Wang, S, and Hazelrigg, T. (1994) *Nature* 369, 400-403), actin Act88F gene (Barthmaier, P. and Fyrberg, E. (1995) *Dev. Biol.* 169, 770-774), and a nuclear localization signal (Davis, I., Girdham, C. H. & O'Farrell, P. H. (1995) *Dev. Biol.* 170, 726-729); of the yeast microtubule and spindle pole associated dis1 gene product (Nabeshima, K., Kurooka, H., Takeuchi, M., Kinoshita, K., Nakaseko, Y., & Yanagida, M. (1995) *Genes Dev.* 9, 1572-1585) and an RNA binding protein Npl3p (Corbett, A. H., Koepp, D. M., Schlenstedt, G., Lee, M. S. Hopper, A. K. & Silver, P. A. (1995) *J. Cell Biol.* 130, 1017-1026); and of a mammalian ion channel protein, NMDAR1 (Marshall, J., Molloy, R., Moss, G. W., Howe, J. R. & Hughes, T. E. (1995) *Neuron* 14, 211-215), microtubule-associated protein, MAP4 (Olson, K. R., McIntosh, J. R. & Olmsted, J. B. (1995) *J. Cell Biol.* 130, 639-650), and a secretory protein, chromogranin B (Kaether, C. & Gerdes, H. H. (1995) *FEBS Lett.* 369, 267-271) have been constructed fused to GFP. However, none of these chimeric proteins have been to transcription factors or co-factors and no suggestions have been made as to the usefulness of such a fusion to study physiologically relevant interaction on an amplified DNA target. Furthermore, none of these reports indicated a successful use of GFP in mammalian cells.

Many human diseases result from aberrant steroid function, and many disease states, i.e., inflammation, are treated with glucocorticoid and other steroid derivatives. A large number of drugs have been developed whose function is based on the ability to interact with and activate steroid receptors. The identification and characterization of these compounds is a laborious, time-consuming and expensive process involving years of work. Even with a large investment of resources, the true behavior of these compounds in living cells is not understood.

The present invention allows observation for the first time of in vivo target sites within a higher eukaryotic nucleus for trans-regulatory molecules, such as transcription factors, e.g., glucocorticoid receptor (GR). The visualization of physiologically relevant in vivo target sites for any transcription factor to date has not previously been accomplished. The present invention provides a powerful method for identification of any single target site in a higher eukaryotic genome, comprising roughly 60,000-80,000 genes (Bird, A. P. (1995) *Trends Genet.* 11:94-100), using a singly fluorescently-labelled regulatory factor, which has not been considered previously. Discriminating direct versus indirect interaction between a regulatory molecule and its putative regulatory site is critical for the development of highly specific drugs directed against trans-regulatory factors. Traditionally, the methodology for showing potentially direct interactions involves nuclease or chemical protection experiments and transient co-transfection experiments of the putative regulator and its regulated site. While this approach indicates potential direct interaction, it does not necessarily imply direct interaction. Alternatively, the approach of making compensatory mutations between the regulatory sequences as well as the DNA binding specificity has been used in an attempt to demonstrate direct regulatory interaction (Schier, A. F. and Gehring, W. J. (1992) *Nature* 356:804-807), an extension of the principles of second site suppression in genetics to molecular biology. However, such an approach makes enormous assumptions of our understanding of sequence-specific recognition by sequence-specific DNA binding proteins in vivo, which certainly would not be valid for many systems, since many profound developmental events are governed by exquisite interactions to fine tune the system regarding, for example, concentration gradients of trans-regulatory factors. The present invention allows a simple and straight-forward manner in which direct interaction between a sequence-specific DNA binding protein or its co-factor and its putative regulatory site in the in vivo genomic context can be addressed. With this simple inventive methodology, novel classes of drugs directed not only against members of the steroid-ligand-dependent transcription factors but to new classes of drugs that target other transcription factors or their co-factors can be screened.

Additionally, the present invention provides the first opportunity to observe and monitor gene targeting specifically of steroid receptors in living cells wherein binding of the steroid receptor to its response element target can be observed distinctly from translocation of steroid receptor. The invention therefore provides for many relevant analyses, such as real-time determination of steroid activity in subjects as well as screening of compounds for response element binding/targeting capabilities as distinct from translocation capabilities. Such methods have implications in many diseases associated with steroid hormones, such as endocrine disorders, rheumatic disorders, collagen diseases dermatological diseases, allergic states, ophthalmic diseases, respiratory disease, hematologic disorders, neoplastic disease, edematous states, gastrointestinal diseases and neurological conditions, and in other uses such as prevention of rejection of transplanted tissues.

SUMMARY OF THE INVENTION

The present invention provides a mammalian cell having a plurality of steroid receptor response elements in an array such that the response element can be directly detected when bound by fluorescently labeled steroid receptor.

The present invention further provides a chimeric protein comprising a fluorescent protein fused to a transcription factor. The present invention also provides a chimeric protein comprising a fluorescent protein fused to a steroid receptor.

The instant invention provides an isolated nucleic acid encoding a chimeric protein comprising a fluorescent protein fused to a transcription factor and an isolated nucleic acid encoding a chimeric protein comprising a fluorescent protein fused to a steroid receptor.

The instant invention also provides a cell containing a nucleic acid encoding a chimeric protein comprising a fluorescent protein fused to a transcription factor and a cell containing a nucleic acid encoding a chimeric protein comprising a fluorescent protein fused to a steroid receptor.

The instant invention provides a method of screening for a compound that binds to a selected nucleic acid comprising:
  a. contacting compound fluorescently labeled by a fluorescent protein with a cell having a plurality of copies of the nucleic acid in an array such that the nucleic acid can be directly detected when bound by fluorescently labeled compound; and
  b. directly detecting the location of fluorescence within the cell, fluorescence aggregated at the site of the nucleic acid array indicating a compound that binds to the selected nucleic acid.

The present invention also provides a method of characterizing a ligand's effect on cellular localization of a compound to which the ligand binds in a cell comprising:
  a. contacting the ligand with a cell having the compound fluorescently labeled by a fluorescent protein and
  b. directly detecting the location of fluorescence within the cell, the location of fluorescence in the cell indicating the localization effect of the ligand on the compound.

Additionally provided is a method of determining a binding site for a DNA-binding protein comprising:
  a. contacting the DNA-binding protein fluorescently labeled by a fluorescent protein with a cell having a plurality of copies of a nucleic acid having a putative binding site in an array such that the putative binding site can be directly visualized when bound by the fluorescently labeled DNA-binding protein, and
  b. directly detecting the location of fluorescence within the cell, the presence of fluorescence aggregated at the putative binding site indicating a binding site to which the DNA-binding protein binds.

The present invention also provides a method of screening for a ligand that activates gene targeting of a steroid receptor in the nucleus of a mammalian cell comprising:
  a. contacting the ligand with a mammalian cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor; and b. directly detecting the location of fluorescence within the cell, fluorescence aggregated at the site of the steroid receptor response element array in the nucleus indicating a ligand that activates the gene targeting of a steroid receptor in the nucleus of a mammalian cell.

The present invention provides a method of screening for a ligand that activates the translocation of a steroid receptor to the nucleus in a mammalian cell comprising:
 a. contacting the ligand with a mammalian cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor; and
 b. directly detecting the location of fluorescence within the cell, the location of fluorescence aggregated in the nucleus indicating a ligand that activates the translocation of a steroid receptor to the nucleus in a mammalian cell.

The instant invention provides a method of detecting in a biological sample the presence of an agonist of a steroid receptor comprising:
 a. contacting the sample with a mammalian cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor; and
 b. directly detecting the location of fluorescence within the cell, the location of fluorescence aggregated at the site of the steroid receptor response element array in the nucleus indicating the presence of an agonist of the steroid receptor in the sample.

The present invention also provides a method of detecting in a biological sample the presence of an antagonist of a steroid receptor comprising:
 a. contacting the sample and an agonist of the steroid receptor with a mammalian cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor; and
 b. directly detecting the location of fluorescence within the cell, the absence of fluorescence substantially aggregated at the site of the steroid receptor response element array in the nucleus indicating the presence of an antagonist of the steroid receptor in the sample.

The present invention provides a method of monitoring the level of an agonist of a steroid receptor in a subject comprising:
 a. periodically obtaining a biological sample from the subject,
 b. contacting the sample with a mammalian cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor; and
 c. directly detecting the location of fluorescence within the cell, a decrease in fluorescence aggregated at the site of the steroid receptor response element in the nucleus in a later-obtained sample relative to an earlier-obtained sample indicating a decrease in level of the steroid agonist of the steroid receptor in the sample and an increase in fluorescence aggregated at the site of the steroid receptor response element in the nucleus in a later-obtained sample relative to an earlier-obtained sample indicating an increase in level of the steroid agonist of the steroid receptor in the sample.

The instant invention provides a method of monitoring the balance between levels of an agonist of a steroid receptor and an antagonist of the steroid receptor in a subject comprising:
 a. periodically obtaining a biological sample from the subject,
 b. contacting the sample with a mammalian cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor; and
 c. directly detecting the location of fluorescence within the cell, an increase in fluorescence aggregated at the site of the steroid receptor response element in the nucleus in a later-obtained sample relative to an earlier-obtained sample indicating an increase in level of the steroid agonist relative to level of the steroid antagonist in the sample, and a decrease in fluorescence aggregated at the site of the steroid receptor response element in the nucleus in a later-obtained sample relative to an earlier-obtained sample indicating an increase in level of the steroid antagonist of the steroid receptor relative to level of the steroid agonist in the sample.

The instant invention also provides a method of determining an effective dosage of a steroid receptor agonist in a subject comprising:
 a. transferring into a set of cells from the patient a nucleic acid encoding a chimeric protein comprising a fluorescent protein fused to a steroid receptor;
 b. contacting the cells in the set with one of a selected range of dosages of the steroid agonist; and
 c. directly detecting location of fluorescence in the set of cells, a dosage capable of locating fluorescence substantially in the nucleus indicating an effective dosage of steroid receptor agonist.

The present invention provides a method of determining an effective dosage of a steroid receptor agonist to maintain steroid receptor activation for a selected period of time in a subject comprising:
 a. administering to the subject a dosage of the steroid receptor agonist,
 b. periodically obtaining a biological sample from the subject,
 c. contacting the sample with a mammalian cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor; and
 d. directly detecting the location of fluorescence within the cell, a dosage that maintains the location of fluorescence at the site of the steroid receptor response element array in the nucleus for the selected period of time indicating an effective dosage.

The present invention also provides a method of determining an effective dosage of a steroid receptor antagonist to abrogate agonist activity for a selected period of time in a subject comprising:
 a. administering to the subject a dosage of the steroid receptor agonist,
 b. periodically obtaining a biological sample from the subject;
 c. contacting the sample with a mammalian cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor; and
 d. directly detecting the location of fluorescence within the cell,
a dosage that prevents the location of fluorescence at the site of the steroid receptor response element array in the nucleus for the selected period of time indicating an effective dosage.

The present invention also provides a method of detecting a defect in a response pathway of a steroid receptor in a subject comprising transferring into a cell from the subject a nucleic acid functionally encoding a chimeric protein comprising a fluorescent protein fused to the steroid receptor and detecting the location of fluorescence within the cell as compared to the location of fluorescence within a normal, control cell transfected with the nucleic acid, a difference in location of fluorescence within the cell of the subject as compared to location of fluorescence within the normal, control cell indicating a defect in the response pathway of the steroid receptor.

The instant invention provides a method of determining whether a defect in a response pathway of a steroid receptor in a subject is in translocation of the steroid receptor to a cell nucleus, comprising transferring into a cell from the subject having the defect a nucleic acid functionally encoding a chimeric protein comprising a fluorescent protein fused to the steroid receptor and detecting the location of fluorescence within the cell, the location of fluorescence substantially in the cytoplasm of the cell indicating the defect is in translocation of the steroid receptor to the nucleus.

BRIEF DESCRIPTION OF THE DRAWINGS

FIG. 3 shows the construction of GFP-GR.

DETAILED DESCRIPTION OF THE INVENTION

Figure 1:
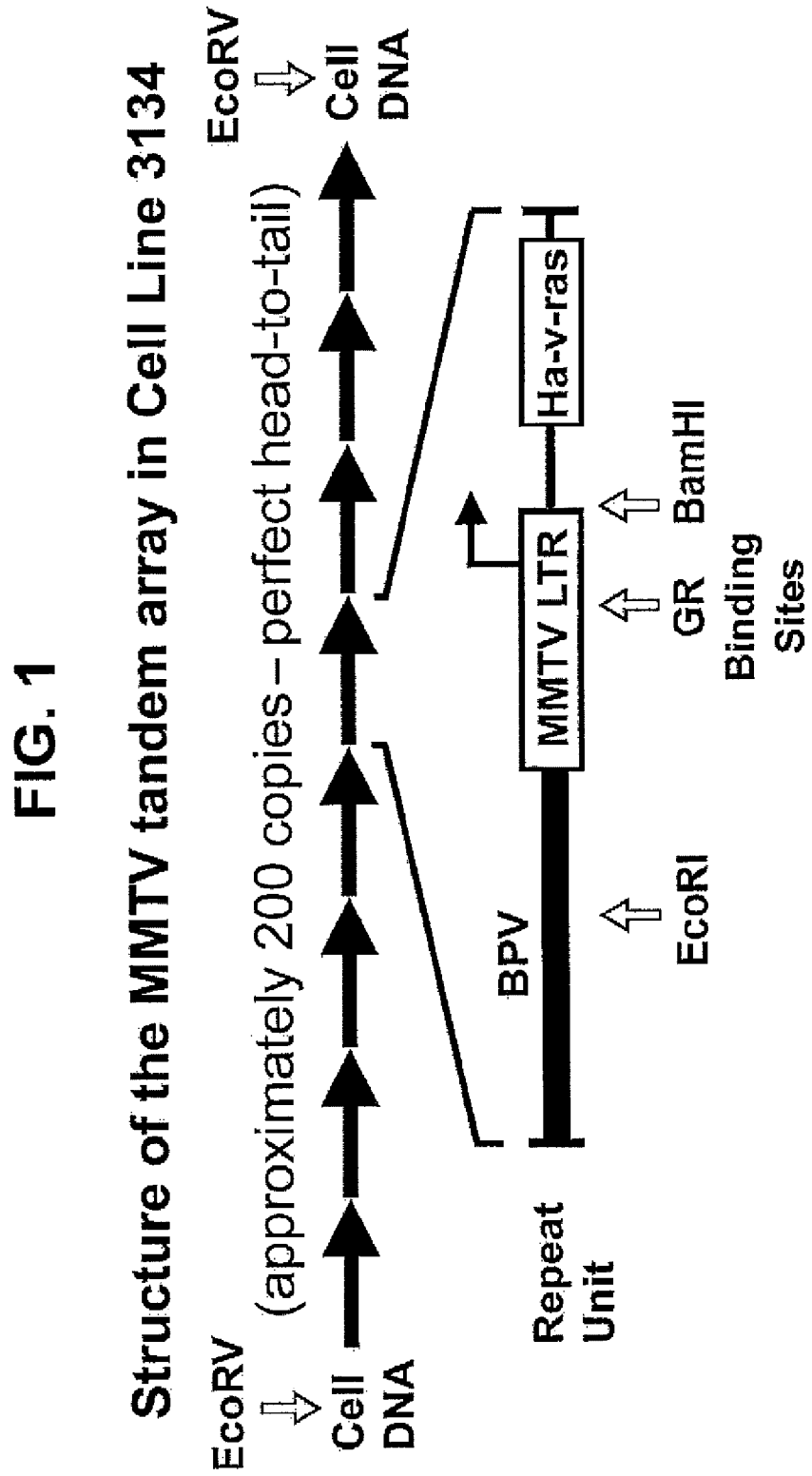
FIG. 1 is a diagram of the integrated, tandem array of bovine papilloma virus (BPV) 69% transforming fragment, mouse mammary tumor virus (MMTV) long terminal repeat (LTR) containing glucocorticoid receptor (GR) binding sites, and, Harvey murine sarcoma virus v-ras sequences (Ha-v-ras).

The present invention provides cell lines such as the murine cell line 3134, that contains a set of mouse mammary tumor virus (MMTV) Harvey murine sarcoma virus (HaMuSV) v-ras sequences organized in a head-to-tail tandem array of approximately 200 copies. Each MMTV promoter sequence in this array contains 4 glucocorticoid receptor (GR) binding sites; the complete array thus contains nearly 1000 GR binding sites. This cell is used to visualize directly the interaction between GR and its binding site in chromatin in living cells. This is accomplished with a fluorescent labeled copy of the GR. This array thus provides the unique opportunity to visualize direct receptor/target interactions. This structure, for which there is no precedent, provides for the first time a reagent to observe the interaction of steroid receptors with their response elements in living cells, and to characterize the effectiveness of medically important steroid ligands in activating gene expression in mammalian cells.

In the present application, we have shown the usefulness of GFP in monitoring the activity of a steroid hormone receptor. The ability to directly observe living cells has allowed us to follow in real time the process of cytoplasm to nuclear translocation, and has revealed for the first time differences in GR intranuclear accumulation pattern dependent on the type of activating ligand. Furthermore, the patterns of GR accumulation are remarkably similar between adjacent cells, suggesting an order in the organization of the interphase nucleus. This ability to observe living cells has also revealed subcellular localization of partially activated estrogen receptor (ER). Thus, the use of GFP has revealed new details about steroid localization and organization of the eukaryotic nucleus.

As used in the specification and in the claims, "a" can mean one or more, depending upon the context in which it is used.

The present invention provides reagents and methods for detecting, by direct visual evaluation, the binding of fluorescently labelled compounds to a nucleic acid. This direct detection can be accomplished by the use of a cell line having a sufficient number of copies of the binding region of the nucleic acid in an array, such as tandem repeats, that allows detection of the array when a fluorescently labeled compound is bound to the binding region by direct detection of the fluorescence localized at the site in the cell nucleus of the nucleic acid array. For example, after binding, cells can immediately, without further treatment of the cells, be placed under a fluorescent microscope and fluorescence directly visualized. Thus compounds can be rapidly analyzed for binding capability in a manner that clearly depicts the binding. Importantly, the binding detected in this assay is biologically relevant. The detected event represents receptor mobilization to a correct genetic target in the living cell. Thus, interactions revealed with this assay are much more reliable as measures of biologically germane receptor activity. Additionally, analyses of levels of compounds or defects in pathways involving the binding of such compounds to their nucleic acid binding site in specific subjects can be performed, as further described below.

Any selected nucleic acids and binding sites, and compounds that may bind thereto, either directly or indirectly, can be analyzed by this method, in a desired cell, as elaborated below. For example, binding of any transcription factor to its activation site on a nucleic acid can be directly determined along with the proteins associated with the factor (e.g., co-activator, co-repressor, adapter, or molecules in a similar category). Additionally, for example, binding of any selected steroid receptor can be directly detected and analyzed for both translocation to the nucleus and binding to the corresponding response element(s) in the nucleus. Thus, compounds typically can be proteins, polypeptides and peptides; however, other compounds can include, for example, Peptide Nucleic Acids (PNAs), antisense nucleic acids and organic molecules (e.g., dexamethasone). Importantly, for any compound, the step of binding to the binding site can visually be distinguished from the step of translocation to the nucleus, or alternatively, exit from the nucleus.

In general, the present invention utilizes fluorescent labeling of the compound by a fluorescent protein, as fluorescent protein is herein described, adding the labeled compound to cells, and directly detecting the location and/or aggregation of fluorescence in the cells. For detection of the translocation of the labeled compound to the nucleus, any cell can be utilized, since the resulting location of fluorescence can be visualized as either in the cytoplasm or in the nucleus. Additionally, for such detection events, cells having increased copy number of the binding site, in any array, can be used. For detection of binding to the target nucleic acid site, the present invention provides cells having a plurality of nucleic acid binding sites in an array such that the nucleic acid binding site can be directly detected when bound by binding compound, such as a ligand, transcription factor, etc., fluorescently labeled by a fluorescent protein, as described herein.

As used herein, direct detection means defection of the fluorescence emitted from the site in the cells when excited by light, ultraviolet or visible, without the need for any additional chemical reactions or treatment of the cells. The fluorescence is directly detected by any device capable of detecting fluorescence, such as a fluorescent microscope, as visualized by the eye of the operator of the microscope at the time or as recorded from the microscope such as by photography of the field of view or through the use of photosensitive detectors. A fluorescent microscope, such as a confocal laser scanning microscope or an epifluorescent microscope, can be used, as is known in the art. There is no requirement that cells be, e.g., fixed or stained or contacted by any additional reagents, in order to detect the binding. Thus living cells can be assayed, and results obtained, immediately after binding. Therefore, for example, subjects can be advised immediately of results of analyses as described below. Furthermore, it is anticipated that screening of both nuclear localization of fluorescence (translocation) and focal localization of fluorescence on a target array will be adapted to high volume computerized image analysis. That is, the analysis of large numbers of samples will be automated for either the repetitive examination of clinical samples or the large-scale screening of compounds in the research environment.

The cell can be derived from any desired mammal, such as, for example, human, monkey, mouse, hamster and rat. The nucleic acid can be amplified in an appropriate array by any of several means, as known to those skilled in the art. Generally, a selected nucleic acid binding site or collection of sites, for example as found within the context of a transcriptional regulatory-region, i.e., promoters, enhancers silencers, etc., can be amplified in an array detectable by the present means, for example, by gene amplification of the nucleic acid binding site (e.g., the steroid receptor response element or the transcription factor binding site) by linking it to a gene readily amplified in a tandem array, for example, dihydrofolate reductase, or by multimerization of the nucleic acid binding site or sites by synthetic DNA synthesis and/or enzymatic synthesis, for example, through the use of ligase and polymerases, and introducing the amplified element into selected mammalian cells. Such methods are further elaborated in the examples provided below.

The cells used herein have an array of the nucleic acid having binding sites under analysis such that the nucleic acid can be directly detected when bound by a fluorescently labeled compound. Such array as contemplated herein has sufficient copies of the nucleic acid and in such an arrangement that the fluorescently labeled binding compound, when bound to the site can be directly detected and readily identified. Therefore, the array includes arrangement of the copies in sufficiently close physical proximity along a chromosome, either present endogenously or artificially introduced or induced, or in extrachromosomally replicating episomes, to allow localization of fluorescence at a discrete, detectable site in the nucleus, as seen under standard magnification for cells and nuclei. Such array as contemplated herein allows detection in the context of chromatin, as exists in the interphase nucleus. An example of such an array is a series of direct tandem repeats of the nucleic acid. An example of a tandem array of direct repeating units is depicted in FIG. 1.

By a "plurality" of any herein described nucleic acid having a binding site is meant that the number of copies of the nucleic acid having the binding site (e.g., the steroid receptor response element or the transcription factor binding site) is greater than one. Preferably, the cells have more than about five copies, more preferably more than about ten copies, more preferably more than about twenty, and more preferably more than about forty copies. For example, cell line 3134, described herein, has about two hundred copies of the MMTV LTR-Ha-v-ras-gene, each of which has four copies of the binding site for glucocorticoid receptor and with each site accommodating two glucocorticoid receptor molecules. Any number which allows detection of the site upon binding of the fluorescently labeled binding compound is contemplated. Thus, an example of a cell of the present invention is a cell of the cell line 3134 deposited with American Type Culture Collection as accession number CRL-11998 (ATTC).

Specifically, the present invention provides a cell having a plurality of steroid receptor response elements in an array such that the response element can be directly detected when bound by fluorescently labeled steroid receptor. A response element, as used herein, includes any nucleic acid to which a steroid receptor directly binds, but also includes the steroid receptor associated, either directly or indirectly, factors that are recruited to the vicinity of the element (e.g., nuclear factor 1 (NF1), octomer transcription factor 1 (OTF1), steroid receptor coactivator 1 (SRC1), etc.). Steroid receptors, and corresponding response elements to which they bind, can include any steroid receptor, for example, glucocorticoid receptor, estrogen receptor (ER), progesterone receptor, androgen receptor, mineralocorticoid receptor, vitamin D receptor. Examples of steroid receptor response elements include those contained in the mouse mammary tumor virus (MMTV) long terminal repeat (LTR) (which has binding sites for glucocorticoid receptor, mineralocorticoid receptor, progesterone receptor, and androgen receptor), and those contained in vitellogenin and osteocalcin genes (which have binding sites for estrogen and vitamin D receptors). Thus, response elements in such array in a cell can include other transcriptional regulatory elements contained within the mouse mammary tumor virus long terminal repeat and bovine pappilloma virus 69% transforming DNA. Many steroid receptors and steroid response elements, as exemplified above, are known to the skilled artisan; however, any steroid receptor and its response element is contemplated herein. In addition to steroid receptors, there are other ligand-dependent receptors (such as thyroid hormone receptor, retinoic acid receptor, retinoid X receptor, TCCD (dioxin) receptor, fatty acid activatable receptors, etc.) and stimulus-dependent receptors (such as peroxisome proliferator activated receptor, growth factor-dependent receptors (e.g., epidermal growth factor, nerve growth factor, etc.)), and factors (such as CREB, NFAT, NFkB/IkB, etc.), and other receptors whose ligand remains to be defined (such as mammalian homologs of the *Drosophila* tailless, knirps, sevenup, FTZF1 genes, etc.). Many of these receptors or factors can be found listed in the book [Parker, M. G. (1993) Steroid Hormone Action (Oxford University Press, New York pp. 210)], in a recent review article [Tsai, M. J. & O'Malley, B. W. (1994) *Annu. Rev. Biochem.* 63, 451-486], and in the GenBank database, which will contain additional receptors as well as the complete nucleotide sequences of the genes and cDNAs. In addition, the cell line offers a number of tandemly repeated regulatory sites for sequence-specific transcription factors (such as activating protein 2 (AP2), OTF1, NF1/CTF, etc.) as well as general transcription factors (such as TFIID, initiator protein, etc.). The steroid receptor response elements (or other transcriptional regulatory elements) used in the present invention in arrays detectable as described herein can be integrated into the genome of the cell, maintained in the cell on artificial mammalian chromosomes (Monaco, A. P. and Larin, Z. (1994) *Trends Biotechnol.* 12, 280-286) or can be carried on episomal elements.

The cell can further comprise a nucleic acid encoding a chimeric protein wherein a fluorescent protein is fused to the steroid receptor. Steroid receptors as described above are contemplated for use in a chimeric protein. Typically, the steroid receptor in the chimeric protein encoded by the nucleic acid in a selected cell is one that binds to the response element in the selected cell in the herein described array. Throughout this application by "a fluorescent protein" is meant a protein that fluoresces in cells without adding exogenous cofactors. That is, it is a protein that can be expressed in cells and detected in these cells simply by exciting the protein with light and visualizing the resultant fluorescence. An example of such a fluorescent protein is the green fluorescent protein (GFP) originally isolated from the jellyfish *Aequorea victoria*. Another example of a fluorescent protein as defined herein is the green fluorescent protein originally isolated from *Renilla reniforms*, which demonstrated a single absorption peak at 498 nm and an emission peak at 509 nm. (Cubitt, et el. (1995) TIBS 20: 448-455). By fluorescent protein is also contemplated that modifications may be made to a fluorescent protein, as long as the resulting protein fluoresces when expressed in cells. Modifications can be developed based upon the chemistry of chromophore formation. (Cubitt, et al. TIBS 20: 448-455). Generally, however, one may prefer to leave the glycine which participates in forming the chromophore, in part by cyclization of a Ser-Tyr-Gly moiety (Gly 67 in *Aequorea* GFP in the Ser65-Tyr66-Gly67 moiety), intact. An example of a useful substitution that modifies the absorption spectra is the substitution in *Aequorea* green fluorescent protein for serine at amino acid 65 by, for example, threonine, cysteine, leucine, valine, or alanine, that allows the excitation of the chromophore at a lower energy (longer wavelength) than the naturally occurring protein thereby greatly decreasing the destruction of the chromophore as occurs when it is excited at a higher energy. Such mutation at amino acid 65 also increases brightness and rate of oxidation as compared to wild-type *Aequorea* GFP when each is excited at its longest wavelength peak. In addition, other spectral variants of GFP, such as improved blue variants of GFP have been developed (e.g. pCI-nGL2-C656G; pCI-nGL3-C656G; pCI-nGL4-C656G; pCI-nGL5-C656G; pCI-nGL7-C656G; pCI-nGL9-C656G; pCI-nGL10-C656G; pCI-nGL111-C656G). Variants emitting longer wavelengths (e.g., red variants) can also be developed by introducing other mutations into the GFP DNA. Additionally, the codon usage of any GFP-coding sequence can be modified to human codons, according to known methods. For example, pGreenLantern-1 (LifeTechnologies, Inc., Gaithersburg, Md., catalog number 10642-015) is a commercially available S65T variant GFP cDNA with mammalian codon usage. Other commercially available humanized GFP-cDNAs are: pEGFP-N (catalog numbers: 6086-1; 6085-1; 6081-1 from Clontech), pEGFP-C (catalog numbers: 6084-1; 6083-1; 6082-1 from Clontech), and pHGFP-S65T (catalog number 6088-1 from Clontech). Additional useful modifications of any fluorescent protein can include other modifications that speed up the rate of the oxidation step of chromophore formation, that increase brightness at longer wavelengths, and that reduce pohotoisomerization and/or photobleaching. Furthermore, in general it is preferable that GFP not be truncated by more than about one amino acid from the amino terminus and about 10-15 amino acids from the carboxyl terminus. Detection of additional fluorescent proteins can readily be performed by standard approaches such as searching for proteins having some homology to GFP in nucleic acid libraries from organisms that demonstrate fluorescence by nucleic acid hybridization and by searching for homologous nucleic acids and proteins in other organisms in databanks of nucleic acid and protein sequences and testing the encoded proteins for fluorescence. It is possible that forced protein evolution of the currently existing GFP can be achieved by randomizing the entire GFP coding region so as to make every single possible change at every single amino acid coding region as well as pairs and further combination of changes. Desirable changes yielding better chromophore or different excitation/emission spectra can be characterized by fluorescence spectroscopy or flow cytometry upon translation of the coding sequences into proteins. An example of one general approach would be to take advantage of the phage display system for expression of the chromophore on the surface of a bacteriophage using a modification of what is currently being done for antibodies (e.g. Pharmacia Biotech, Inc.'s Recombinant Phage Antibody System). Another general approach would be to adapt a protocol similar to that used to select novel enzymatic activities displayed by RNAs (Bartel, D. P. and Szostak, J. W. (1993) *Science* 261, 1411-1418) for selection of novel fluorescent proteins.

Therefore, also provided herein are chimeric proteins comprising a fluorescent protein fused to a transcription factor, and nucleic acids encoding such proteins. One example of a transcription factor that can be used herein, described in further detail above, is a steroid receptor; however, numerous other transcription factors can be utilized. For example, basal transcription factors (e.g. TFIID, etc.), and sequence specific DNA binding transcription factors (e.g., AP1, AP2, SP1, NF1, etc). Additional transcription factors are listed in, for example, computer databases such as that maintained by the National Center for Biotechnology Information (NCBI, Bethesda, Md.) accessible through the BLAST program (see item 19 (TFD) for transcription factors; item 20 for eukaryotic promoter sequences). Additionally, as used in the claims, "transcription factors" include transcription adaptor molecules or cofactors, which localization within the cell can be monitored also by this method. Transcription adaptor molecules or cofactors are those molecules that interact with transcription factors to effect their function (i.e., their activation or repression functions). For example, SRC1, steroid receptor coactivator 1, is a cofactor of steroid receptors.

The chimeric protein can include a linking peptide sequence between the fluorescent protein and the steroid receptor. For example, a sequence of the amino acids glycine and alanine, or a sequence of alanine alone can be used; however, any sequence of amino acids and any length can be used that does not interfere with the binding of the steroid receptor to its response element and that does not prevent fluorescence of the fluorescent protein. Typically, a linker peptide will range from two to about ten amino acids but maybe shorter or longer. Of course, certain linker peptides maybe preferred over others, e.g., the presence of four basic amino acids in a string of six might suffice as a nuclear localization signal so as to mislocate the uninduced state of the factor. A linker peptide can be used to separate the fluorescent protein structurally from the response element and can function to allow the fluorescent protein independently of the remaining portion of the chimeric protein. An example of a chimeric protein, which has GFP fused via five glycine-alanine repeating units to the N-terminus of the glucocorticoid receptor, is provided herein as SEQ ID NO: 2. Typically, a fluorescent protein can be fused to either the C-terminus or the N-terminus of the transcription factor; however, the preferable construction for a specific transcription factor can readily be determined. Linker peptides can readily be introduced between the two proteins in the chimeric protein by producing an nucleic acid that encodes the chimeric protein having the linker sequence between the fluorescent protein and transcription factor components.

Modifications to the fluorescent protein portion of the chimeric protein and/or the transcription factor, e.g., steroid receptor can be made. For example, a green fluorescent protein can be modified as described above. The transcription factor, for example, can be modified to increase or decrease its affinity for its binding site or to determine if a selected modification affects its binding affinity. In the case of steroid- or ligand-dependent transcription factor, the region involved in steroid- or ligand-binding can be altered to either increase or decrease the affinity to the steroid or ligand or alter the specificity of the ligand. Furthermore, other functions of the factor, such as transactivation potential, maybe modified. An example of such a modification is found in the chimeric protein having the amino acid sequence set forth in SEQ ID NO: 2, wherein the transcription factor is glucocorticoid receptor having a substitution of serine for cysteine at amino acid 656 that has a higher binding affinity for its ligand than the protein having the naturally occurring amino acid sequence. This substitution also increases the transactivation potential of the receptor, resulting in "superactivation." This cysteine 656 mutation can be utilized, for example in rat, human and mouse glucocorticoid receptor. For example, steroid receptors, or any transcription factor, can be modified in their steroid binding domains to increase affinity for steroid, thus allowing one to increase use of exogenous receptor over endogenous receptor in a cell.

The transcription factor of the chimeric protein can be derived from any selected mammal. Additionally, chimeric proteins utilizing a transcription factor from one mammal can often be used in a cell from another mammal. For example, the glucocorticoid receptor amino acid sequence is highly conserved, particularly in the binding region among rat, human and mouse, and, for example, the rat glucocorticoid receptor binds with high affinity to the human glucocorticoid response element.

Also provided in the present invention is nucleic acid encoding a chimeric protein wherein a fluorescent protein is fused to a transcription factor. The nucleic acid encoding the chimeric protein can be any nucleic acid that functionally encodes the chimeric protein. For example, to functionally encode, i.e., allow the nucleic acid to be expressed, the nucleic acid can include, for example, expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from metallothionine genes, actin genes, immunoglobulin genes, CMV, SV40, adenovirus, bovine papilloma virus, etc. A nucleic acid encoding a selected chimeric protein can readily be determined based upon the genetic code for the amino acid sequence of the selected chimeric protein, and, clearly, many nucleic acids will encode any selected chimeric protein. Modifications to the nucleic acids of the invention are also contemplated, since mutations in the steroid receptor binding can thereby be studied for binding affinity. Additionally, modifications that can be useful are modifications to the sequences controlling expression of the chimeric protein to make production of the chimeric protein inducible or repressible upon addition to the cells of the appropriate inducer or repressor. Such means are standard in the art (see, e.g., Sambrook et al., *Molecular Cloning: A Laboratory Manual,* 2nd Ed., Cold Spring Harbor Laboratory, Cold Spring Harbor, N.Y., 1989). The nucleic acids can be generated by means standard in the art, such as by recombinant nucleic acid techniques, as exemplified in the examples herein, and by synthetic nucleic acid synthesis or in vitro enzymatic synthesis.

An example of a nucleic acid of the present invention is a nucleic acid encoding a chimeric protein comprising a green fluorescent protein fused via ten amino acid gly-ala linker to the N-terminus of the rat glucocorticoid receptor. One nucleic acid encoding this nucleic acid is set forth in SEQ ID NO: 1. This nucleic acid encodes a modified. *Aequorea victoria* green fluorescent protein and a modified rat glucocorticoid receptor. Another example is a nucleic acid encoding a chimeric protein comprising a modified *Aequorea victoria* green fluorescent protein fused (via ten amino acid gly-ala linker) to the N-terminus of the human estrogen receptor.

Additionally contemplated by the invention are closely related receptors and nucleic acids encoding them. Thus, provided by the invention are nucleic acids that specifically hybridize to the nucleic acids encoding the chimeric proteins under sufficient stringency conditions to selectively hybridize to the target nucleic acid. Thus, nucleic acids for use, for example, as primers and probes to detect or amplify the target nucleic acids are contemplated herein. Typically, the stringency of hybridization to achieve selective hybridization is about 5° C. to 20° C. below the Tm (the melting temperature at which half of the molecules dissociate from its partner). Hybridization temperatures are typically higher for DNA-RNA and RNA-RNA hybridizations. The washing temperatures can similarly be used to achieve selective stringency, as is known in the art. (Sambrook et al., *Molecular Cloning: A Laboratory Manual,* 2nd Ed., Cold Spring Harbor Laboratory, Cold Spring Harbor, N.Y., 1989; Kunkel et al. *Methods Enzymol.* 1987-154. 367, 1987).

The present invention provides cells containing a nucleic acid of the invention. A cell containing a nucleic acid encoding a chimeric protein typically can replicate the DNA and, further, typically can express the encoded protein. The cell can be a prokaryotic cell, particularly for the purpose of producing quantities of the nucleic acid, or a eukaryotic cell, particularly a mammalian cell. The cell is preferably a mammalian cell for the purpose of expressing the encoded protein so that the resultant produced protein has mammalian protein processing modifications. Additionally, as described above, the cell can have an array of a nucleic acid to which the encoded chimeric protein binds.

Labeled compounds and nucleic acids encoding chimeric proteins can be delivered into cells by any selected means, in particular depending upon the purpose of the delivery of the compound and the target cells. Many delivery means are well-known in the art. For example, electroporation, calcium phosphate precipitation, microinjection, cationic or anionic liposomes, and liposomes in combination with a nuclear localization signal peptide for delivery to the nucleus can be utilized, as is known in the art. In particular for transfer of a nucleic acid into a cell, to enhance transfer a cotransfection of the nucleic acid with a second nucleic acid encoding a selectable marker can be performed, and transfected cells selected for by the selectable marker. For example, the interleukin 2 receptor (IL2R) gene can be cotransfected, and selection performed by using beads having the antibody to IL2R bound to the beads to separate out transfected cells. Such methods are standard in the art.

Nucleic acids of the present invention can be used to generate transgenic animals in which the nucleic acid encoding a selected chimeric protein, such as GFP-GR for GR studies or GFP-ER for ER studies, is added to the germ line of the animals. Thus a cell of the invention containing an nucleic acid of this invention is contemplated to include a cell in a transgenic animal. With such transgenic animals, cytoplasm-to-nucleus translocation and gene targeting can be observed in any tissue of interest. Thus studies over the life cycle of the animal can be conducted, so that, for example, development and effects of environment, aging, cancer, etc. can be readily observed. Transgenic animals are generated by standard means known to those skilled in the art.

The provision of the present method to visualize physiologically relevant target sites within the eukaryotic nucleus allows one to directly observe nuclear target sites for any desired steroid- or ligand-dependent transcription factors as well as any nuclearly targeted trans-regulatory factors. Conceptually, the requirements are: 1) to tag the protein of interest with a fluorescent protein, such as the green fluorescent protein, using standard recombinant DNA techniques wherein the two cDNAs are fused in frame to each other such that introduction back into the mammalian cell would give rise to the synthesis of the chimeric protein of interest; and, 2) to create an identifiable nuclear target site by linking together multiple copies of the potential target site to generate a large enough array as to be readily discernible when the fluorescently labeled chimeric protein interacts with the target site. Such an interaction is visible as an intense, concentrated fluorescent signal unique to the cell harboring the array and absent from the parental cell lacking the array. Agents which modify the interaction of the labeled factor with its cognate site can thus be readily screened.

The present invention further provides a method of screening for a compound that binds to a selected nucleic acid comprising:
 a. contacting compound fluorescently labeled by a fluorescent protein with a cell having a plurality of copies of the nucleic acid in an array such that the nucleic acid can be directly detected when bound by fluorescently labeled compound; and
 b. directly detecting the location of fluorescence within the cell,
fluorescence aggregated at the site of the nucleic acid array indicating a compound that binds to the selected nucleic acid. Thus, the present method can be utilized to directly determine whether a compound binds a nucleic acid, directly or indirectly. For example, transcription factors that have been indirectly shown to affect binding can now be assessed to determine if they do bind the target DNA. If by this method a factor labeled by a fluorescent protein, as herein described (for example, *Aequorea* GFP), is added to cells, and upon visualization of the fluorescence, the fluorescence is seen to be aggregated at the site of the target array of nucleic acid, then the factor, or a factor(s) to which the labeled factor binds, binds the nucleic acid. The nucleic acids are conceptualized as merely serving as an easily identifiable "stage" upon which the "actors" (i.e., transcription factors and associated factors) appear.

In the present inventive methods, by fluorescence aggregated at the site of the nucleic acid array is meant fluorescence aggregated at a single predominant site within the nucleus. Such aggregation can readily be detected upon excitation of the fluorescent protein. Detection, as described above, can be performed with the use of a fluorescent microscope. Magnification can be altered as desired for more or less detail in visualizing the aggregation, such as from about 60× to about 200×, with a typical magnification being about 100×. The fluorescent protein in any herein described method can be, for example, a green fluorescent protein, as described herein.

Compounds for use in the present methods can be labeled by standard means in the art for linking a peptide to the compound. For example, when the compound to be labeled is a peptide, polypeptide or protein, a chimeric protein can be made by synthesizing a nucleic acid that encodes the chimeric protein having the fluorescent protein fused to the compound protein. Proteins can also be labeled with a fluorescent protein by a chemical bridge. Additionally, a fluorescent protein label can be placed on the compounds by non-covalent interaction, such as that displayed by steroids with their binding domain [e.g., fluorescein or rhodamine conjugated dexamethasone (available through Molecular Probes, Inc. catalog number D-1382 or D-1383) for the glucocorticoid receptor].

More than one chimeric protein, preferably each comprising a fluorescent protein that emits a different wavelength of light (for example a modification of *Aequorea* GFP that emits blue and a modification of *Aequorea* GFP that emits green), can be used simultaneously in the present inventive methods. For example, plasmids pCI-nGL2-C656G; pCI-nGL3-C656G; pCI-nGL4-C656G; pCI-nGL5-C656G; pCI-nGL7-C656G; pCI-nGL9-C656G; pCI-nGL10-C656G; pCI-nGL11-C656G, all GFP-GR having blue variants of GFP (BFP) in a humanized codon usage (improved blue variants) can be used with any GFP-GR having green GFP (such as pCI-nGFP-C656G, pCI-nGL1-C656G, pTET-nGFP-C656G and pOP-nGFP-C656G, exemplified herein) in this method.

Alternatively, two different fluorescent moieties that show distinct excitation maxima with identical emission wavelengths could also be simultaneously utilized to detect the presence of both fluorescently labeled compounds on the same DNA array. With the appropriate combination of fluorescent molecules only one excitation wavelength may be required to detect the presence of both fluorescent moieties in close proximity through the process of fluorescent energy transfer, wherein the excitation wavelength excites one moiety which emits at the absorption wavelength of the second moiety. Such simultaneous use will allow the detection of interaction of various transcription factors and cofactors with each other and with the DNA to activate and/or repress transcription from a specific regulatory sequence.

Cells for use in the present methods are cells having a plurality of copies of the nucleic acid in an array such that the nucleic acid can be directly detected when bound by fluorescently labeled compound. Such cells are described herein and can be prepared as described herein. An example of such a cell is cell line 3134, having about two hundred copies of the MTV LTR-Ha-v-ras-gene, each of which has four copies of the binding site for glucocorticoid receptor, in direct tandem repeats integrated into the genome of the cell. Cells further can have a nucleic acid encoding a chimeric protein comprising a fluorescent protein fused to the binding compound/ transcription factor of interest, i.e., the binding compound/ transcription factor which may bind the nucleic acid in the array in the cell. For example, 3134 cells containing pCI-nGFP-C656G, pCI-nGFP-C656G, pTET-nGFP-C656G or pOP-nGFP-C656G are exemplified herein. Nucleic acids encoding a chimeric protein can either be integrated or not, as best suits the specific method being performed.

The present invention also provides a method of characterizing cells in which a compound fluorescently labeled by a fluorescent protein is expressed in the cell and the localization of the fluorescent protein observed for perturbation in localization of the fluorescently labeled protein in the absence or presence of signals that affect protein function (example of GFP-ER in the MCF7 and MDA-MB-231 cell line).

The present invention also provides a method of screening for a ligand that activates gene targeting of a steroid receptor in the nucleus of a mammalian cell comprising contacting the ligand with a cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor; and directly detecting the location of fluorescence within the cell, fluorescence aggregated at the site of the steroid receptor response element array in the nucleus indicating a ligand that activates the gene targeting of a steroid receptor in the nucleus of a mammalian cell. A ligand for any steroid receptor can be determined by this method by creating an array of the steroid receptor response element in the cell used. For example, cell line 3134 can be used to detect ligands that activate gene targeting of glucocorticoid response element, progesterone receptor, or aldosterone receptor. An example of a chimeric protein for use in this method in, for example cell line 3134, is one that has a green fluorescent protein, such as *Aequorea* fluorescent protein, fused to the N-terminus of glucocorticoid receptor, such as the chimeric protein comprising the amino acid sequence set forth in SEQ ID NO: 2.

The present invention further provides a method of screening for a ligand that activates the translocation of a steroid receptor to the nucleus or redistribution of a steroid receptor in a mammalian cell comprising contacting the ligand with a cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor; and directly detecting the location of fluorescence within the cell, change in the location of the fluorescence (e.g., cytoplasm to nucleus in the case of the glucocorticoid receptor or redistribution within each cellular compartment; e.g., for primarily nuclear receptors, such as the progesterone receptor, aggregation on the MMTV LTR-array in the 3134 cell) could indicate a potential ligand of the receptor. In the present method, redistribution of the receptor can be directly observed. Also, in the case of the glucocorticoid receptor, translocation to the nucleus, even in the absence of binding to the nuclear DNA, can be seen, and importantly, one can see if a ligand causes only translocation to the nucleus (by location of fluorescence primarily in the nucleus, but in a diffuse or reticular, rather than aggregated, pattern) or causes both translocation to the nucleus and binding to nuclear DNA (by location in the nucleus aggregated primarily at a site). In the case of estrogen receptor which has been partially activated due to trace estrogenic substances present in the culturing media, the receptor is nuclearly localized but shows dramatically different intranuclear distribution in two human breast cancer cell lines. In the case of MCF7 cell, a human adenocarcinona breast cell line which contains endogenous estrogen receptor and shows hormone dependent growth, the GFP-tagged estrogen receptor is collected upon nuclear structures and shows focal accumulation patterns. In contrast, the MDA-MB-231 cell, a human adenocarcinoma breast cell line which lacks endogenous estrogen receptor and shows hormone-independent growth, the GFP-tagged estrogen receptor under the same culturing condition is extremely diffuse. These two dramatic differences in the nuclear localization patterns in two different human breast cancer cell lines suggests potential usefulness of GFP-ER as a diagnostic reagent for characterizing different human breast cancer cells as well as characterizing the progression of human breast cancer. These differences in GFP-ER localization patterns also suggest an additional requirement for cellular components in permitting the targeting of the estrogen receptor onto nuclear structures; these cellular components maybe absent as the cell progresses from hormone-dependent to a hormone-independent stage in the progression of human breast cancer.

The present invention additionally provides a method of detecting in a biological sample the presence of an agonist of a steroid receptor comprising contacting the sample with a cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor; and directly detecting the location of fluorescence within the cell, the location of fluorescence aggregated at the site of the steroid receptor response element array in the nucleus indicating the presence of an agonist of the steroid receptor in the sample.

Biological samples can include any relevant sample from the body, such as blood, plasma, urine and saliva.

The present invention also provides a method of detecting in a biological sample the presence of an antagonist of a steroid receptor comprising contacting the sample and both agonist and antagonist of the steroid receptor with a cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor; and directly detecting the location of fluorescence within the cell, the absence of fluorescence substantially aggregated at the site of the steroid receptor response element array in the nucleus indicating the presence of an antagonist of the steroid receptor in the sample.

Also provided is a method of monitoring the level of an agonist of a steroid receptor in a subject comprising periodically obtaining a biological sample from the subject, contacting the sample with a cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor, and directly detecting the location of fluorescence within the cell, a decrease in fluorescence aggregated at the site of the steroid receptor response element in the nucleus in a later-obtained sample relative to an earlier-obtained sample indicating a decrease in level of the steroid agonist of the steroid receptor in the sample and an increase in fluorescence aggregated at the site of the steroid receptor response element in the nucleus in a later-obtained sample relative to an earlier-obtained sample indicating an increase in level of the steroid agonist of the steroid receptor in the sample.

Further, provided by the present invention is a method of monitoring the balance between levels of an agonist of a steroid receptor and an antagonist of the steroid receptor in a subject comprising periodically obtaining a biological sample from the subject, contacting the sample with a cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor; and directly detecting the location of fluorescence within the cell, an increase in fluorescence aggregated at the site of the steroid receptor response element in the nucleus in a later-obtained sample relative to an earlier-obtained sample indicating an increase in level of the steroid agonist relative to level of the steroid antagonist in the sample, and a decrease in fluorescence aggregated at the site of the steroid receptor response element in the nucleus in a later-obtained sample relative to an earlier-obtained sample indicating an increase in level of the steroid antagonist of the steroid receptor relative to level of the steroid agonist in the sample.

The present invention also provides a method of determining an effective dosage of a steroid receptor agonist in a subject comprising transferring into a set of cells from the patient a nucleic acid encoding a chimeric protein comprising a fluorescent protein fused to a steroid receptor; contacting the cells in the set with one of a selected range of dosages of the steroid agonist; and directly detecting location of fluorescence in the set of cells, a dosage capable of locating fluorescence substantially in the nucleus indicating an effective dosage of steroid receptor agonist.

Further provided by the present invention is a method of determining an effective dosage of a steroid receptor agonist to maintain steroid receptor activation for a selected period of time in a subject comprising administering to the subject a dosage of the steroid receptor agonist; periodically obtaining a biological sample from the subject; contacting the sample with a mammalian cell having a plurality of steroid receptor response elements in an array such that the response element can be directly detected when bound by fluorescently labeled steroid receptor and the cell further comprising a nucleic acid encoding a chimeric protein wherein a fluorescent protein is fused to the steroid receptor; and directly detecting the location of fluorescence within the cell, a dosage that maintains the location of fluorescence at the site of the steroid receptor response element array in the nucleus for the selected period of time indicating an effective dosage.

The present invention additionally provides a method of detecting a defect in a response pathway of a steroid receptor in a subject comprising transferring into a cell from the subject a nucleic acid functionally encoding a chimeric protein comprising a fluorescent protein fused to the steroid receptor and detecting the location of fluorescence within the cell as compared to the location of fluorescence within a normal, control cell transfected with the nucleic acid, a difference in location of fluorescence within the cell of the subject as compared to location of fluorescence within the normal, control cell indicating a defect in the response pathway of the steroid receptor.

The present invention also provides a method of determining whether a defect in a response pathway of a steroid receptor in a subject is in translocation of the steroid receptor to a cell nucleus, comprising transferring into a cell from the subject having the defect a nucleic acid functionally encoding a chimeric protein comprising a fluorescent protein fused to the steroid receptor and detecting the location of fluorescence within the cell, the location of fluorescence substantially in the cytoplasm of the cell indicating the defect is in translocation of the steroid receptor to the nucleus.

The present invention also provides a method of characterizing a ligand's effect on cellular localization of a compound to which the ligand binds in a cell comprising contacting the ligand with a cell having the compound fluorescently labeled by a fluorescent protein and directly detecting the location of fluorescence within the cell, the location of fluorescence in the cell indicating the localization effect of the ligand on the compound. Compounds can be, e.g., steroid receptors, transcription factors and the like. For example, the examples provide characterization of localization of GR in response to two ligands, dexamethasone and RU486, and characterization of the localization of ER in response to ligands, agonist beta-estradiol or anti-estrogens, 4-hydroxytamoxifen or ICI164384." By this method, the ligands triggering binding of so-called "orphan receptors" to their binding site(s) can be discovered.

Additionally provided is a method of determining a binding site for a DNA-binding protein comprising contacting the DNA-binding protein fluorescently labeled by a fluorescent protein with a cell having a plurality of copies of a nucleic acid having a putative binding site in an array such that the putative binding site can be directly visualized when bound by the fluorescently labeled DNA-binding protein, and directly detecting the location of fluorescence within the cell, the presence of fluorescence aggregated at the putative binding site indicating a binding site to which the DNA-binding protein binds. The absence of fluorescence aggregated at the putative binding site can suggest a binding site to which the DNA-binding protein does not significantly bind. the location of fluorescence in the cell indicating the localization effect of the ligand on the compound.

Also provided by the present invention is a method for screening for gene-specific combinations of compounds that bind the gene specifically, comprising contacting (a) a first compound labeled by a fluorescent protein emitting a first spectrum of light and a second compound labeled by a fluorescent protein emitting a second spectrum of light with (b) a cell having a plurality of copies of the regulatory region of the gene in an array such that the regulatory region can be directly detected when bound by compound labeled by a fluorescent protein. Fluorescence for the first- and second spectrum is then localized. Aggregation of fluorescence of both the first and second spectrum at the site of the regulatory region array would indicate a combination of compounds that binds the gene specifically; the location of only one spectrum aggregated at the array would indicate that only the corresponding compound binds the gene of interest directly. By using a combination of screens, compounds that bind the specific DNA both directly and indirectly can be determined for a gene of interest. Such gene-specific combinations of compounds can be used to develop gene-specific drugs that interfere with transcription activators in a selective manner. This method is based on the fact that each transcription factor, cofactor, etc. affects many genes, but for each gene there is likely only one combination of factors and cofactors that activates/represses it. Therefore, once, by this screening method, it has been determined which combination of factors causes activation or repression of a specific gene, then a combination of drugs, to affect all relevant factors for that specific gene, can be administered to selectively activate/repress that gene. Thus a combination of drugs can ultimately be used to activate or repress the selected gene.

Statement Concerning Utility

The present invention provides methods for directly detecting the binding of compounds to nucleic acids. The present invention allows a simple and straightforward manner in which direct interaction between a sequence-specific DNA binding protein or its co-factor and its putative regulatory site in the in vivo genomic context can be addressed. For example, GFP-steroid fusion proteins and cell lines containing receptor binding sites (response elements) in multimerized arrays are provided for direct visualization of in vivo gene targeting. These reagents provide a simple, rapid, straightforward, sensitive, and biologically relevant assay for each target nucleic acid and binding compound. These reagents can in turn be used for several medically important applications, including diagnostic tests for concentration of cognate ligand in clinical samples (urine, saliva, blood, etc.). Additionally, the reagents can be used for direct tests for defects in steroid pathways in subjects. The reagents further can be used for screening of chemical banks for compounds with ligand agonist activity for each receptor, and development of drugs based on these activities. Furthermore, using the fluorescent protein-steroid receptor fusions, colocalization of a selected receptor with any other cofactor that may be recruited to the chromosome template can be evaluated. Using a separate tag (different color) for the DNA target, the steroid receptor can be fused to any factor that may be recruited by the steroid receptor and determine if the factor colocalizes on the DNA target when the steroid receptor is activated, allowing for a direct test for defects in factor colocalization in human disease/syndromes. This ability to observe direct interaction of any trans-regulatory factor or co-factor and its regulatory site in vivo provides a screening method for useful and novel drugs, directed against trans-regulators, and the development of gene-specific multi-drug therapies. Using the glucocorticoid receptor as an example and known ligands of the receptor (e.g., agonist dexamethasone and antagonist RU486), the validity of the methodology is herein demonstrated. In a specific example, the ability to monitor effective hormone concentration by this novel methodology in real time can lead to the development of diagnostic kits that can be used to properly gauge the required amounts of hormone administered to patients requiring long-term or short-term hormone treatment. In addition, in the case of those trans-acting factors regulated at the level of the nuclear/cytoplasmic and cytoplasmic/nuclear translocation step, diseases arising from such a failure can be directly diagnosed by fusion of the regulatory molecule to a fluorescent moiety using standard recombinant DNA techniques. With this simple, inventive methodology, novel classes of drugs directed not only against members of the steroid-ligand-dependent transcription factors but to new classes of drugs that target other transcription factors or their co-factors can be screened. Furthermore, by using combination of drugs which target certain trans-regulatory factors either specifically or selectively, a gene-specific based drug therapy regimen can be created. This multi-drug therapy designed against a certain critical gene implicated for a particular human disease would be tailored to affect the activity of the trans-regulatory factors all of which act synergistically to regulate the transcription of the gene implicated in the disease. Furthermore, the reagents allow the development of transgenic animals containing fusion proteins such as each of the GFP-receptor fusions that can provide a unique tool to study subcellular distribution of the receptors in all tissues of the animal, and the effect of pharmacologic agents on function of each of the receptors in the various tissues. Numerous other utilities will be apparent to the skilled artisan in light of the present invention.

EXAMPLES

The present invention is more particularly described in the following examples which are intended as illustrative only since numerous modifications and variations therein will be apparent to those skilled in the art.

Plasmids.

pCI-nGFP-C656G: Plasmid pCI-nGFP-C656G was derived from pCI-nH6HA-C656G (Smith et al., submitted) and pZA69 (a kind gift from Mike Moser and Ravi Dahr). pZA69 contains a BspHI fragment of pZA66, a plasmid containing S65T GFP (Tsien, R. Y. (1995) *Nature* 373, 663-664) with the internal NcoI site removed by a silent mutation. The pCI-nH6HA-C656G DNA expresses the rat glucocorticoid receptor with the C656G mutation (kindly provided by S. Simons, Jr.) under the control of the CMV promoter/enhancer, and is tagged at the N-terminus with $(his)_6$ and hemagglutinin epitope recognized by monoclonal antibody 12CA5 (Niman, H. L., Houghten, R. A., Walker, L. E., Reisfeld, R. A., Wilson, I. A., Hogle, J. M. & Lerner, R. A. (1983). *Proc. Natl. Acad. Sci. U.S.A.* 80±4949-4953); this DNA was cleaved at a unique site with PvuII, separating the two tags from the rest of the glucocorticoid receptor. A 768 bp DNA fragment containing the GFP cDNA with the S65T mutation was inserted at the PvuII site. This GFP DNA fragment is obtained by digesting pZA69 with BglI, attaching a BglI hairpin linker with the sequence (5'-GCGCGCTGATCA-GAATTCCTTTTAGGAATTCTGATCAGCGCGCTGA-3') (SEQ ID NO:3), recutting the resulting DNA with BclI and XhoI, and then filling-in with the large fragment of DNA polymerase (Klenow) to create a 768 bp blunt-end fragment.

pCI-nGL1-C656G: The GFP (S65T) variant with the jellyfish codon usage in the mammalian expression GFP-GR vector, pCI-nGFP-C656G, has been replaced with a humanized codon usage from the plasmid, pGreenLantern-1 (LifeTechnologies, Inc., Gaithersburg, Md., catalog number 10642-015), for improved translation in mammalian cells [this humanized GFP is also approved for in vitro diagnostic use by LifeTechnologies] to generate an improved mammalian expression GFP-GR plasmid, pCI-nGL1-C656G.

pCI-nGL2-C656G; pCI-nGL3-C656G; pCI-nGL4-C656G; pCI-nGL5-C656G; pCI-nGL7-C656G; pCI-nGL9-C656G; pCI-nGL10-C656G; pCI-nGL11-C656G: Blue variants of GFP (BFP) in a humanized codon usage (improved blue variants) have been generated which are fused to the rat glucocorticoid receptor (C656G). Each has a different chromophore. Site-directed mutagenesis of the GFP element of pCI-nGL1-C656G (which has humanized GFP) was performed to introduce known chromophore-altering mutations into the GFP element. Site-directed mutagenesis was performed using Chameleon™ double-stranded site-directed mutagenesis kit (Stratagene, catalog number 200509). These new fusion plasmids were then expressed in 1471.1 cells. Fluorescent spectrophotometry indicates the chromophores are present and that the GFP-GR fusion is intact. Additional mutants, such as those producing a longer wavelength chromophore, e.g. red chromophores, can be made by the same methods.

GFP-ER plasmid: The glucocorticoid receptor portion of pCI-nGL1-C656G DNA has been replaced with a human estrogen receptor (ER). ER binds to an ER response element in cells. The GFP-ER was found to be functional in both transcriptional activation as well as proper subcellular localization in several cell lines, as described below. GFP-ER plasmid is made using the same site-directed mutagenesis as for preparing blue variant plasmids. Briefly, a cDNA encoding ER is inserted into pCI-nGL1-C656G in place of the GR cDNA. An ER cDNA (Green, Stephen, et al., Nature 320:134-139 (1986) (GenBank accession number X03635) (note: this sequence has a $Gly_{400}$ to $Val_{400}$ mutation); Greene, Geoffrey L., et al *Science* 231:1150-1154 (1986) (GenBank accession number M12674 (having $Gly_{400}$ to $Val_{400}$ mutation)); Pfeffer, U. *Cancer Res.* 53:741-743 (1993) (GenBank accession number X73067) (ER fragment having correct $Gly_{400}$ region coding sequence)) is mutagenized to create a MluI site at the start point of translation of ER and a SalI site in the 3' untranslated region of the cDNA (alternatively, the ER sequence can be generated by PCR). pCI-nGL1-C656G has a unique BssHII site after the (gly-ala)5 linker and a SalI site after the GR portion of the plasmid DNA The DNA cut end made by MluI is complementary to the end made by the BssHII. Therefore, the GR cassette can be removed by BssHII/SalI digestion and the ER cassette (released by MluI/SalI digestion) subcloned into the remaining vector at the BssHI and SalI cut ends.

pOP-nGFP-C6M656G: The original cDNA encoding GFP-GR from the plasmid, pCI-nGFP-C656G, has been subcloned into a tetracycline-regulatable mammalian expression vector, pTET-Splice (LifeTechnologies, catalog number 10583-011), to give pTET-nGFP-C656G, and a lac-regulatable mammalian expression vector, pOPRSVI CAT (Stratagene Cloning Systems, catalog number 217450) to give pOP-nGFP-C656G.

Other plasmids used in this study are: pLTRLuc (full-length MMTV LTR driving the expression of a luciferase gene) (Lefebvre, P., Berard, D. S., Cordingley, M. G. & Hager, G. L. (1991) *Mol. Cell. Biol.* 11(5), 2529-2537), pCMVIL2R (IL2R expression plasmid) (Giordano, T., Howard, T. H., Coleman, J., Sakamoto, K. & Howard, B. H. (1991) *Exp Cell Res.* 192, 193-197), and pUC18 (Life Technologies, Inc.).

GFP-fusion plasmids of the invention are tested for expression and subcellular localization by transfection into several mammalian cells. For example, GFP-GR plasmids were analyzed in C127 (mouse) cells, HeLa (human cervical cancer) cells, and MCF7 (human breast adenocarcinoma) cells (ATCC accession number HTB22). GFP-ER plasmids were analyzed in 1471.1 cells, C127 (mouse) cells, MCF7 (human breast adenocarcinoma) cells, and MDA-MB-231 (human breast adenocarcinoma) cells (ATCC accession number HTB 26). Localization is observed in the absence of added hormone in either-5% or 10% charcoal-stripped fetal calf serum. Cells having GFP-fusion plasmids are then treated with a selected ligand, and subcellular localization and quantitative observations are made.

Cell Line 1471.1 and Derivatives

Cell line 1471.1 contains multiple copies of a BPV MMTV-LTR-chloramphenicol acetyltransferase (CAT) reporter gene fusion introduced in the murine adenocarcinoma C127 cell (Archer, T. K., Cordingley, M. G., Marsaud, V., Richard-Foy, H. & Hager, G. L. (1989) in *Proceedings: Second International CBT Symposium on the Steroid/Thyroid Receptor Family and Gene Regulation*, eds. Gustafsson, J. A., Eriksson, H. & Carlstedt-Duke, J. (Birkhauser Verlag A G, Berlin), pp. 221-238).

Derivatives of 1471.1 cells which contain over a thousand copies of the MMTV LTR-CAT have also been generated with the tetracycline- and lac-regulatable GFP-GR (pTET-nGFP-C656G and pOP-nGFP-C656G), e.g., cell line 3677. In these derivative cell lines, GFP-GR expression occurs upon tetracycline withdrawal from 5 ug/ml or upon induction with IPTG using standard procedures and as recommended by the manufacturer of these inducible systems.

Transfection. Plasmid DNA was transiently introduced into 1471.1 cells either by calcium phosphate coprecipitation using a BES-based buffer (Chen, C. & Okayama, H. (1987) *Mol. Cell Biol.* 7, 2745-2752) or by electroporation. For calcium phosphate coprecipitation, semi-confluent cells maintained in Dulbecco's modified eagle media (DMEM; Life Technologies, Inc.) supplemented with 10% fetal calf serum (FCS; Life Technologies, Inc.), 2 mM glutamine, and 50 mg/ml gentamicin sulfate were trypsinized, washed, resuspended at $7 \times 10^4$ cells/ml in DMEM supplemented as above except FCS was treated with charcoal/dextran-treated fetal bovine serum (Hyclone Laboratories, Inc.), dispensed as 1 ml into $2 \times 2$ cm² Lab-Tek Chamber Slide (Nunc, Inc.) or as 10 ml into a 100 mm petri dish layered with 24.5 mm-diameter Dvorak-Stotler coverslips (Nicholson Precision Instrument). Cells were grown overnight in a 37° C. humidified incubator with 5% $CO_2$. The following morning, media was replaced with fresh supplemented DMEM containing dextran/charcoal treated FCS, and in the afternoon, cells were transfected with 1 ml of transfection mixture containing, 20 µg plasmid DNA (as indicated in the appropriate figure legend) per 10 ml of cells, essentially as described (Chen, C. & Okayama, H. (1987) *Mol. Cell. Biol.* 7, 2745-2752). Cells were left overnight in a 37° C. humidified incubator with 2.9% $CO_2$. About 12-16 hours after transfection, media was replaced, and the cells were allowed to recover for two hours before further treatment and imaging. For calcium depletion experiments, cells were electroporated with 5-20 µg pCI-nGFP-C656G DNA for $2 \times 10^7$ cells in 0.2 ml cold DMEM at 250 V and 800 µF, left to recover on ice for 5 minutes, and then diluted in DMEM supplemented with dextran/charcoal treated FCS before plating. Cells were then grown for 12 to 16 hours in a 37° C. humidified incubator at 5% $CO_2$. Before treatment and imaging, cells were fed with fresh media.

Enrichment of Transfected Cells and Analysis of Cytosolic Extracts. Cells that took up exogenous DNA were enriched by cotransfection with pCMVIL2R, an IL2R (interleukin 2 receptor) expression plasmid, and selection for IL2R⁺ cells using magnetic beads (Dynal) coated with mouse anti-human IL2R antibody (Boehringer Manneheim, clone 3G10), as described (Giordano, T., Howard, T. H., Coleman, J., Sakamoto, K. & Howard, B. H. (1991) *Exp Cell Res.* 192, 193-

197). Extracts from the IL2R$^+$ and IL2R$^-$ cells were made by three cycles of freezing and thawing of the cell suspension in either 100 mM sodium phosphate (pH 7.8) with 1 mM DTT or 250 mM Tris-HCl (pH 7.8). After clarifying the lysate, extracts made with the phosphate buffer was used to assay for the amount of luciferase activity in a MicroLumat LB96P as recommended by the manufacture, EG&G Berthold. For the Tris-buffered extract, CAT activity was assayed as described (Gorman, C. M., Moffat, L. F. & Howard, B. H. (1982) *Mol. Cell. Biol.* 2, 1044-1051). Protein concentration was determined by the method of Bradford using the Bio-rad Protein Assay reagent (Bio-rad Laboratories. Inc.).

Determination of Intracellular Calcium. Intracellular free calcium concentrations were determined in single cells by measuring the signal from the calcium sensitive indicator Fura-2, according to Tsien and Harootunian (Tsien, R. Y. & Harootunian, A. T. (1990) *Cell Calcium* 11, 93-109). Briefly, cells were cultured on cover slips and electroporated with the GFP-GR chimera one day before microscopy. In preparation for imaging, cells were treated for 30 min with either assay buffer (Hank's balanced salt solution without phenol red, with 2 mg/ml glucose and 1 mg/ml BSA, containing 3 mM Ca$^{++}$) or with calcium-free buffer (Eagle's No. 2 medium without calcium, containing 1 mg/ml BSA, 5 mM EGTA, 5 µM thapsigargin, 2 µM ionomycin). The cells were then loaded with 5 µmol/L Fura-2-AM (from Molecular-Probes Inc.) and 0.02% pluronic F-127 with either calcium-free or calcium supplemented media (30 min at room temperature, washed three times, then incubated for 15 min at 37° C.). After loading, cells were placed into a Dvorak-Stotler chamber (inner volume 224 µl) and perfused at 37° C. with either calcium-containing or calcium-free media. Intracellular calcium content was measured in three independent experiments—at least 20 cells in each experiment. Ratio imaging was performed using Image 1 software (Universal imaging Corp.) running on an IBM PC, using 340 nm and 380 nm excitation, 510 nm emission, and 490 nm dichroic barrier filters, a Zeiss Photomicroscope III microscope, enclosed into a temperature controlled incubator, and an intensified (Videoscope) CCD camera (Dage 72), and optical disc recorder (Panasonic). The system was calibrated for [Ca$^{2+}$]$_i$ measurement using Fura-2 pentapotassium salt and calibration buffer kit from Molecular Probes Inc. Intracellular free calcium concentrations in cells with calcium supplemented buffer were 350±183 nM, while in calcium-free buffer 60±11 mM.

Image Acquisition and Analysis. For time course studies, cells were placed into a Dvorak-Stotler chamber (inner volume 224 µl) and perfused at 37° C. with assay buffer for 3 min, then with the same buffer containing 1 nM dexamethasone (dex) for 2 hours at 10 ml/hour flow rates. Samples were evaluated using a Zeiss Axiovert 10 microscope surrounded by an incubator and equipped for epifluorescence with illumination from XBO burner, 480 nm excitation and 535 nm emission and 505 nm dichromatic barrier filters (from Chroma Technology Corp.). Images were acquired every 15 seconds with a high resolution, cooled CCD camera equipped with an electromechanical shutter (Photometrics p200). Images were collected on Silicon Graphics workstations (4D310-VGX), using custom software, incorporating functions from a vendor supplied library (G. W. Hannaway & Assoc.). Experiments requiring real time image acquisition were performed on the imaging system described for the intracellular calcium measurements.

Confocal laser scanning microscopy was carried out on a Nikon Optiphot microscope equipped with BioRad MRC-600 confocal laser scanning unit, with fluorescent excitation produced by the 488 nm line of a krypton-argon laser, and using a Fluor 100/1.3 oil phase objective. From living cells expressing GFP-GR, serial 0.5 µm optical sections were collected and the digitized images were imported into a Silicon Graphics Indigo 2 workstation. Three dimensional image rendering, analysis and reconstruction was carried out with the ANALYZE software from the Mayo Clinic.

Figure 3A:
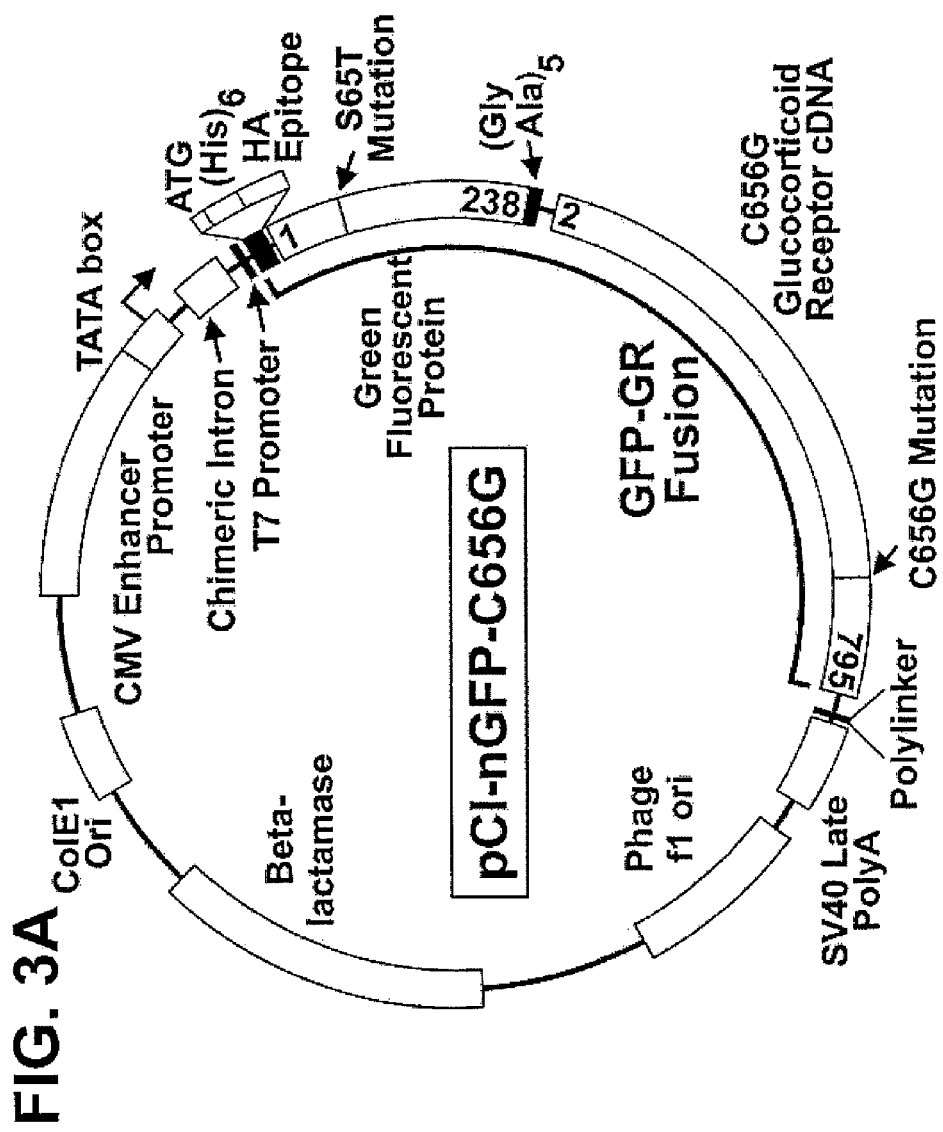
(FIG. 3A) Plasmid pCI-nGFP-C656G contains the green fluorescent protein fused to the C656G mutant glucocorticoid receptor.

Tagging of a Highly Dexamethasone-Sensitive Form of GR with a Highly Fluorescent Variant of GFP. To develop a highly efficient, fluorescent version of the glucocorticoid receptor, we generated a GFP-GR chimera in which cDNA encoding a 27 kDa GFP variant is fused in frame to the second amino acid of a rat glucocorticoid receptor (FIG. 3A). The GFP variant contains a serine to threonine substitution at amino acid 65 (S65T mutation) from the jellyfish *Aequorea Victoria*, which increases the efficiency of formation of the GFP chromophore by accelerating the rate of oxidation required for chromophore generation. In addition, the resulting chromophore is six-fold more fluorescent than the wild-type GFP (Heim, R., Cubitt, A. B. & Tsien, R. Y. (1995) *Nature* 373, 663-664), making the use of this chromophore perhaps the most sensitive method for labelling proteins (Wang, S. & Hazelrigg, T. (1994) Nature 369, 400-403). Additionally, the chromophore is formed faster, potentially explaining its expression at 37° C. in mammalian cells is achieved herein, contrary to reports that the GFP chromophore does not form at a relatively high temperature of 37° C. (Ogawa, et al. *Proc. Natl. Acad. Sci. USA* 92:11899-11903 (1995)).

Since glucocorticoid receptor is ubiquitously present in all mouse cells and selective activation of the tagged receptor is required to assess the functionality of the receptor, we therefore used a glucocorticoid receptor having a higher affinity for its ligand than the endogenous receptor. To this end, S65T GFP was fused to a rat glucocorticoid receptor that contains a cysteine to glycine mutation at position 656 of the steroid binding domain (Chakraborti, P. K., Garabedian, M. J., Yamamoto, K. R. & Simons, S. S. J. (1991) *J. Biol. Chem.* 266, 22075-22078). This point mutation, C656G, increases the affinity of the receptor ten-fold for its ligand. A dose response curve shows complete activation of GFP-GR at 1 nM dexamethasone and half maximum at 0.1 nM; the endogenous mouse receptor is fully activated at 100 nM dexamethasone with the half maximal stimulation at 10 nM. Thus, presence of the C656G mutation permits selective activation of the transfected chimeric receptor without activation of the endogenous receptor.

Figure 3C:
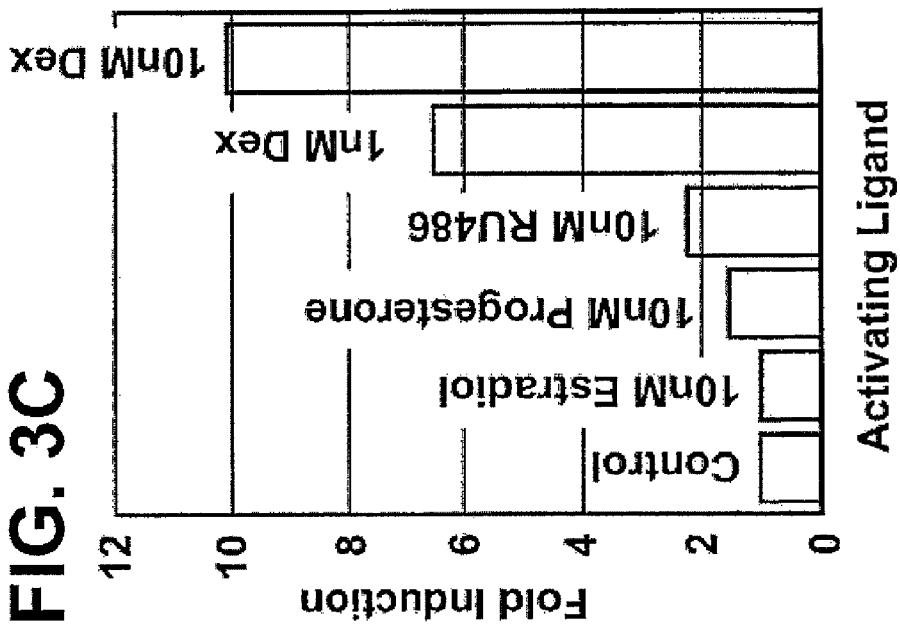
(FIG. 3C) Ligand specificity is presented for activation of endogenous MMTV-LTR-CAT sequences present in the 1471.1 cells. Cells were treated for 4 hrs with the indicated ligand, then harvested and levels of CAT activity determined.
Figure 3B:
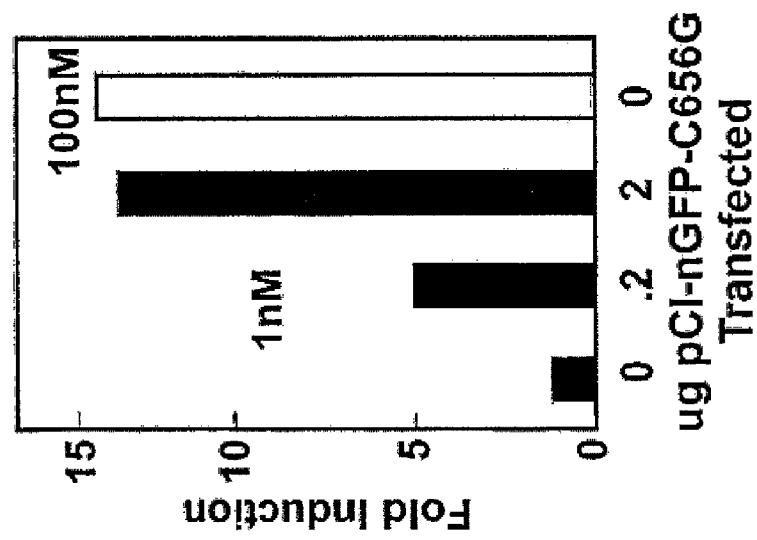
(FIG. 3B) Dexamethasone (dex) dependent stimulation of MMTV-pL-TRLuc is shown for GFP-GR transfected cells. Solid bars represent the IL2R$^+$ selected population activated with 1 nM dex, and the open bar depicts activation of the endogenous receptor with 100 nM dex.

Transcriptional Competence of GFP-GR. When the plasmid encoding this chimera, pCI-nGFP-C656G, is introduced into cultured mouse cells, a fusion polypeptide with the predicted molecular weight of 118 kDa is produced. When these cells are stimulated with 1 nM dexamethasone, a co-transfected reporter construct (pLTRLuc) containing the luciferase reporter gene under the control of the mouse mammary tumor virus promoter (MMTV LTR) is activated (FIG. 3B). In addition, 1 nM dexamethasone-treated cells show accumulation of luciferase activity dependent on the amount of GFP-GR expression plasmid included in the transfection. In the absence of any GFP-GR expression plasmid, no significant luciferase activity accumulated in the 1 nM dexamethasone-treated cells, indicating that 1 nM dexamethasone activated the GFP-GR chimeric protein but not the endogenous GR. With increasing amount of the GFP-GR expression plasmid, luciferase activity in the 1 nM dexamethasone-treated IL2R$^+$ cells reaches the same level as that in 100 µM dexamethasone-treated IL2R$^+$ cells lacking GFP-GR expression plasmid (compare 2 µg pCI-nGFP-C656G, 1 nM dex with 0 µg pCI-nGFP-C656G, 100 nM dex). Since the 100 nM dexamethasone treatment gives complete activation of the endogenous GR in the latter case, we conclude that the GFP-GR chimeric receptor is fully functional in dexamethasone-mediated transcriptional activation of the transiently introduced reporter plasmid DNA.

Furthermore, derivative cell lines of 1471.1 which contain over a thousand copies of the MMTV LTR-CAT have also been generated with the tetracycline- and lac-regulatable GFP-GR (pTET-nGFP-C656G and pOP-nGFP-C656G), allowing GFP-GR expression upon tetracycline withdrawal from 5 ug/ml or upon induction with IPTG using standard procedures and as recommended by the manufacturer of these inducible systems. In these cells, acceptable levels of GFP-GR is reached after overnight induction of the regulatable promoters.

Assay for Ligand Effects: GFP-fusion plasmids of the invention are assayed for effects of a selected ligand on subcellular localization by transfection into selected cells. C127 (mouse) cells, HeLa (human cervical cancer) cells, and MCF7 (human breast adenocarcinoma) cells (ATCC accession number HTB22) were each transfected with GFP-GR plasmids and with GFP-ER plasmids. Localization is first observed in the absence of added hormone in either 5% or 10% charcoal-stripped fetal calf serum. Cells having GFP-fusion plasmids are then treated with a selected ligand, and subcellular localization and quantitative observations are made.

Figure 4A:
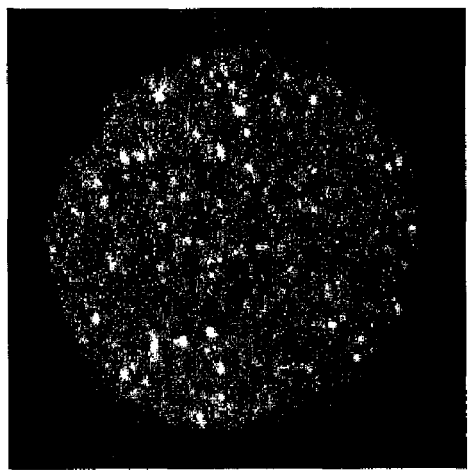
FIG. 4 shows nuclear localization of GFP-GR in MCF7 cells when the cells are treated with (A) dexamethasone or (B) RU486. The fluorescent tag is excited by 489 nm laser light, and the 511 nm emission examined by confocal microscopy, using a standard fluorescein filter set.
Figure 4B:
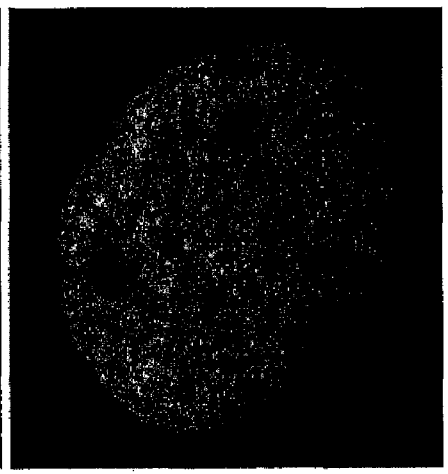

GFP-GR Results: GR is observed to be localized to the cytoplasm in the absence of added ligand. However, when cells having the GFP-GR plasmids were treated with dexamethasone, foci of fluorescent signal (massive variation in the peak and valley of fluorescent signal) were observed in the nucleus (see, e.g., FIG. 4(A)). When these cells were treated with RU486, the fluorescent signal is near uniform, with a matrix-like appearance where fluorescent signal appears (see, e.g., FIG. 4(B)).

Figure 5A:
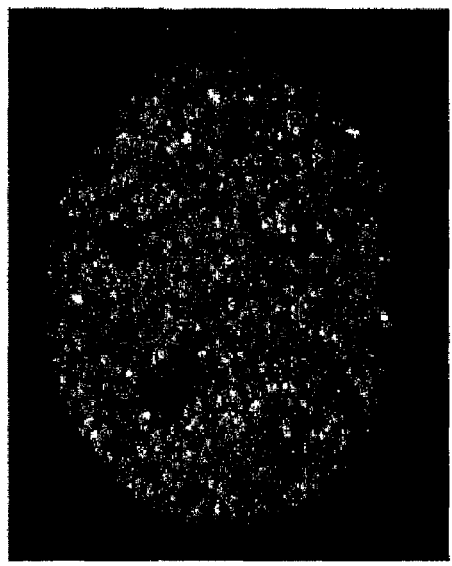
FIG. 5 shows nuclear localization of GFP-ER in (A) MCF7 cells and (B) MDA-MB-231 cells when the fluorescent tag is excited by 489 nm laser light, and the 511 mm emission examined by confocal microscopy, using a standard fluorescein filter set. MCF7 cells are reported to be estrogen receptor positive and hormone dependent. MDA-MB0231 cells are reported to be estrogen receptor negative and hormone independent.
Figure 5B:
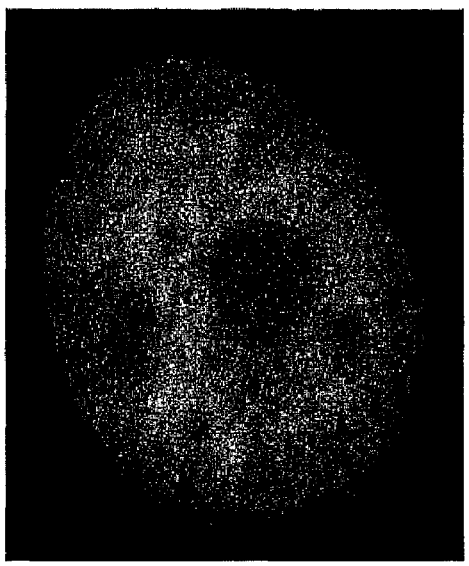

GFP-ER Results: ER is observed to be localized to the nucleus in the absence of added estrogen hormone. When a hormone-dependent, estrogen receptor positive human breast cancer cell line, MCF7, is transfected with GFP-ER expression plasmid, expression of GFP-ER results in nuclear signal that is structured with peaks and valley of concentration of signals (FIG. 5(A)). Although the GFP-ER is already partially activated due to trace estrogenic substances present in the culturing medium, addition of agonist beta-estradiol leads to further concentration of nuclear signals on nuclear structures. In the case of a hormone-independent, estrogen receptor negative human breast cancer cell line, MDA-MB-231, the expressed GFP-ER in the absence of added ligand shows a diffuse, fuzzy pattern, with only hints of attachments to structures in the nucleus.

These results provide an example of use of the present method as a diagnostic for missing, dysfunctional or nonfunctional components in any selected cell. For example, upon determining that a ligand, such as estrogen for ER binding to its response element, is present in a cancer cell and used for growth or maintenance of the cell, one can treat the cancer by administering a compound to deprive the cell of that ligand, such as by administering anti-estrogen to a breast cancer showing the same results as MCF7 (hormone-dependent) to reduce growth of the cells. Similarly, such a diagnostic can tell one if such a treatment in another cell would be futile because the cell is not dependent upon that ligand.

These results also demonstrate that the present method can be used as a screen to classify cell types for the ability (or lack of ability) to target nuclear structures, to traffic compounds in a particular pattern, etc. This also provides information for selecting treatment regimens for various diseases or disorders, based on activating, inactivating or altering the function of ligands in the cell.

Transcriptional activation of the MMTV LTR target genes by GFP-GR shows a ligand specificity characteristic of glucocorticoid receptor. When activated by dexamethasone, GFP-GR is competent to induce not only the transiently introduced MMTV LTR-luciferase reporter DNA, as mentioned above (FIG. 3B), but also the multi-copy MMTV LTR-CAT reporter genes present in 1471.1 cells (1 nM and 10 nM dex, FIG. 3C). In contrast, treatment with 10 nM RU486, an antagonist with little GR agonist activity, or progesterone, a poor agonist, results in little activation of the MMTV LTR-CAT reporter; 17-β-estradiol, a steroid that shows no affinity for GR, fails to activate the LTR. Thus, the ligand specificity of GR in the transcriptional activation of the MMTV LTR is maintained in GFP-GR expressing cells.

Visualization of GFP-GR Cytoplasm-to-Nuclear Translocation in a Single Metabolically Active Cell. Because the S65T variant of the GFP chromophore is resistant to photobleaching (Heim, R., Cubitt, A. B. & Tsien, R. Y. (1995) Nature 373, 663-664), it was possible to use confocal and time-lapse video microscopy to observe GFP-GR over extended periods. Using computer controlled high resolution video and confocal laser scanning microscopy, we examined transfected samples for subcellular localization of the chimeric GFP-GR protein. We observed significant fluorescence in the cytoplasm of about ten percent of total cells, approximately the fraction that typically acquires transfected DNA. Thus) the GFP was functional as a chromophore in a majority of the expressing cells in this mammalian system.

Upon exposure to dexamethasone, translocation of GFP-GR occurs in 100% of fluorescing cells, with the rate of cytoplasm-to-nuclear translocation dependent on the concentration of hormone. At 101 nM, complete translocation was induced within 10 min at 37° C., with half maximal nuclear accumulation at 5 min; this rate is consistent with previous findings (Picard, D. & Yamamoto, K. R. (1987) EMBO. J. 6, 3333-3340). The rate of translocation is decreased with 1 nM dexamethasone (complete translocation over 30 min with half maximum at 9-10 min) and further reduced with 0.1 nM dexamethasone (complete translocation within 2 hours with half maximum at 1 hour).

Analysis of a time-lapse series revealed that GFP-GR accumulated along fibrillar structures and in the perinuclear region very rapidly after hormone addition, probably within seconds. Murine adenocarcinoma cells were cultured on cover slips and transfected with GFP-GR fusion chimera one day before microscopy. Cells were placed into a Dvorak-Stotler chamber and perfused at 37° C. with assay buffer for 3 min, then with buffer containing 1 nM dexamethasone for 2 hrs. With real-time imaging, perinuclear accumulation was observed in a pulsatile pattern with 1-2 second intervals between brightness changes. GFP-GR accumulation was more intense along fibrillar structures in the perinuclear region. After 3 min with 1 nM dexamethasone, GFP-GR was noticeably present in the nucleus, but not in the nucleoli. When approximately ⅓ of the protein had been translocated (9-10 min), a punctuate pattern appeared, and translocation was complete after 30 min. During translocation, the cells frequently became rounded, and moved along the long axis of the cell. We observed reduction of the cell surface, as well as the nuclear volume during the translocation. One hour after hormone treatment, the cells reattach and regain a more flattened shape.

Ligand Specificity of Cytoplasm-to-Nuclear Translocation. Cells were treated with buffer (A), 10 nM 17-β-estradiol (B), 10 nM dexamethasone (C), or 10 nM RU486 (D) for 30 min at 37° C. At the end of hormone treatment, images from living cells expressing GFP-GR were visualized with confocal laser scanning microscope as described above. While complete translocation of GFP-GR was observed in all fluorescing cells treated with dexamethasone, other classes of steroid hormones induced GFP-GR translocation to varying extent reflective of the affinity for GR. The glucocorticoid antagonist RU486, known to have a high affinity for GR (Chakraborti, P. K., Garabedian, M. J., Yamamoto, K. R. & Simons, S. S. J. (1991) *J. Biol. Chem.* 266, 22075-22078), was as potent as dexamethasone for induction of translocation. Progesterone, a weak GR agonist, required a concentration 100-fold higher than dexamethasone for translocation; however, approximately ½ of the GFP-GR remained in the cytoplasm. In contrast, 17-β-estradiol, a steroid hormone that does not bind GR, did not cause intranuclear GFP-GR accumulation (10 nM). Thus, GFP-GR maintained ligand-dependent cytoplasm-to-nuclear translocation, with analog specificity identical to that for the untagged GR with the C656G point mutation (Chakraborti, P. K., Garabedian, M. J., Yamamoto, K. R. & Simons, S. S. J. (1991) *J. Biol. Chem.* 266, 22075-22078). Furthermore, while ligand binding may suffice to trigger efficient cytoplasm-to-nuclear translocation, it may not necessarily cause binding of the receptor to its nuclear target and it may cause varying degrees of activation of the target gene.

Role of Intracellular Free Calcium and Energy in GFP-GR Translocation. Two important issues concerning the nuclear import of proteins were also addressed; these include the role of $Ca^{++}$, and the energy requirement of translocation. Intracellular stores of $Ca^{++}$ were depleted by incubating the cells for 1 hour with the endoplasmic reticulum $Ca^{++}$-ATPase inhibitor, thapsigargin, and the calcium ionophore, ionomycin, in calcium-free media (intracellular free calcium content was measured with ratio imaging in Fura-2 loaded cells). The cytoplasmic pattern of GFP-GR was not significantly altered by calcium depletion. When $Ca^{++}$-depleted cells were subsequently exposed to dexamethasone (10 nM for 30 min. at 37° C.) in $Ca^{++}$-free media, the hormone induced complete translocation of GFP-GR, as seen by images taken from living cells with a confocal laser scanning microscope.

To study the energy dependence of ligand binding, cells were exposed to dexamethasone (10 nM) at 4° C.; then hormone was removed and the cells were warmed to 37° C. under continuous monitoring with video-microscopy (cooled CCD camera from Axiovert 10 microscope system). At 4° C., translocation was completely arrested. Rewarming led to complete translocation and reappearance of the focal GFP-GR localization. This experiment indicates that hormone binding to GR in living cells does not require energy in contrast to the energy-dependent step of translocation.

Focal Accumulation of Nuclear GFP-GR Correlates with Transcriptional Activation. When the intranuclear accumulation of GFP-GR is examined in detail, it is readily apparent that the receptor localizes most prominently at specific foci within the nucleus. In addition, there is a low level of accumulation in a diffuse reticular pattern, forming the basis for the nuclear background fluorescence. The number of these focal accumulations are unique to dexamethasone-treated cells and are not observed in 17-β-estradiol- or progesterone-exposed cells. In RU486-treated cells, focal points are not readily discernible. Instead, GFP-GR accumulates in a diffuse pattern with regions of condensation in a reticular pattern, such that regions of bright fluorescence appear thread-like in shape instead of as distinct foci. Depleting intracellular $Ca^{++}$ did not affect the dexamethasone-mediated formation of intranuclear foci. The ability of agonist to induce focal accumulation of GFP-GR correlated strongly with its ability to activate transcription (FIG. 3C). The striking accumulation of dexamethasone-activated GFP-GR into intranuclear foci immediately suggests that a specific architecture may underlie this distribution. To further examine the structure of intranuclear GR binding sites, confocal laser scanning fluorescent microscopy and three dimensional image reconstruction was carried out.

Organized Architecture of Interphase Nuclei as Revealed by GFP-GR.

Three-dimensional architecture of GFP-GR nuclear target sites was analyzed. Serial 0.5 μm sections of nuclei from dexamethasone treated cells were collected with confocal laser scanning fluorescent microscope, digitized images were imported into a Silicon Graphics Indigo 2 workstation, and three dimensional image segmentation, rendering, analysis and reconstruction was carried out with the ANALYZE software. GFP-GR distributions in the nuclei are displayed as pseudocolored, voxel-gradient-shaded, three dimensional projections. Three dimensional image analysis of the points of GR accumulation in dexamethasone-treated cells reveals a non-random distribution of GFP-GR accumulation. Most strikingly, comparison of adjacent cells demonstrates a reproducible pattern of intranuclear structure for GFP-GR accumulation. A predominance of GFP-GR-accumulating foci is observed in the quadrant of the nucleus adjacent to the glass attachment surface of the cell, while a group of large patches of GFP-GR-containing foci are observed in the top half. Nucleolar structures were always devoid of GFP-GR. The nuclear pattern of RU486-treated cells was again strikingly different from dexamethasone-treated cells. Although essentially all of the GFP-GR is translocated, intranuclear RU486-liganded receptor is distributed throughout the nucleus in a reticular pattern but excluding nucleoli.

3134 Cell Line and Derivatives

The 3134 cell line was derived from a mouse line designated 904.1. This cell was established by transfection of a murine mammary carcinoma line (C127) with a plasmid containing three functional segments: a) the bovine papilloma virus (BPV) 69% transforming fragment serves as a replicon in mammalian cells, b) the mouse mammary tumor virus (MMTV) LTR is a steroid responsive promoter and contains the GR binding sites, and c) the Ha-v-ras gene is a transforming oncogene and serves as a reporter for the MMTV promoter.

This plasmid replicates in 904.1 cells as an 9 kb episomal circle. During passage of this cell line, a spontaneous integration event occurred. This event resulted in the integration of a tandem array of the BPV/MMTV-LTR/Ha-v-ras cassette in perfect head-to-tail orientation. The integrated structure is diagrammed in FIG. 2. Standard agarose gel electrophoresis and southern transfer hybridization analysis with a BPV probe (standard gel) was performed. CHEF gel high molecular weight analysis, again with a BPV probe (CHEF gel) was also performed. When the integrated array is digested with a one-cut restriction enzyme, the repeat unit of 8.8 kd is liberated as a single fragment (BamHI). NdeI and EcoRV (both no-cutters for the repeat unit) digestion leads to no digestion in the standard gel; EcoRV liberates a fragment approximately 2.2 megabase pairs in size. Enzymes that cut multiple times (PstI) give rise to the appropriate fragments for the repeat unit. Since the one cutter enzyme releases only one size fragment from the array, the units must be organized in a perfect head-to-tail array.

Derivatives of 3134 cell lines containing pTET-nGFP-C656G and pOP-nGFP-C656G have been generated allowing GFP-GR expression upon tetracycline withdrawal from 5 ug/ml or upon induction with IPTG using standard procedures and as recommended by the manufacturer of these inducible systems, respectively. For example, 3616 is a single cell clone of 3134 with the pTET-nGFP-C656G DNA allowing acceptable level of GFP-GR expression that contains 200 copies of the MMTV LTR-cat-BPV tandem repeats; 3617 is another single cell clone of 3134 with the pTET-nGFP-C656G DNA but where the copy number of the MMTV LTR-cat-BPV tandem repeats dropped from 200 copies to 150 copies upon passage and then increased to about 170 copies in all cells upon further passage; 3596 is a single-cell clone of 134 having 200 copies of the MMTV LTR-cat-BPV repeats and contains pOP-nGFP-C656G DNA; 3597 is a single cell clone of 3134 with 200 copies of the MMTV LTR-cat-BPV repeats and contains pOP-nGFP-C656G DNA. Acceptable levels of GFP-GR is reached in these derivatives after overnight induction of the regulatable promoters, e.g., after withdrawal of tetracycline in the case of 3616 and 3617, and after addition of IPTG in the case of 3596 and 3597.

Gene Targeting with GFP-GR in 3134 Cell

When the GFP-Glucocorticoid Receptor is transfected into the 3134 cell line, it is initially localized completely in the cytoplasm of the cell, as is normal, non-derivatized glucocorticoid receptor. When GFP-GR is activated with the GR ligand dexamethasone, the receptor translocates to the nucleus and accumulates on the BVP/MMTV-LTR/ras tandem array.

Figure 2:
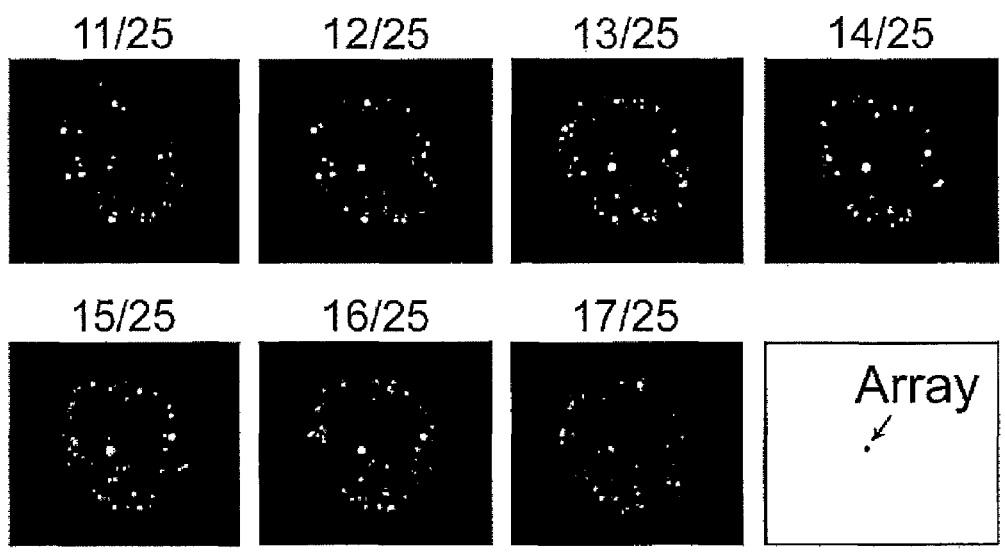
FIG. 2 shows, in panels 11-17, the appearance of GFP-GR when the fluorescent tag is excited by 489 nm laser light, and the 511 nm emission examined by confocal microscopy, using a standard fluorescein filter set. Individual sections are depicted for a representative 3134 cell nucleus. As one focuses on 0.18 micrometer sections throughout the nucleus, a continuous fiber of intense light emission is detected over 5-7 sections, which corresponds to GFP-GR binding to the continuous BVP/MMTV-LTR/ras array. The array is seen in sections 12-16. Below the panels is provided a schematic presentation of the appearance of GFP-GR when the fluorescent protein is excited.
Figure 2:
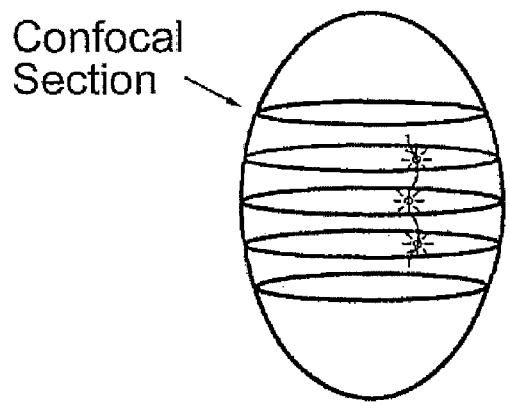

FIG. 2 is a schematic representation of the appearance of GFP-GR when the fluorescent tag is excited by 489 nm laser light, and the 511 nm emission examined by confocal microscopy, using a standard fluorescein filter set. Individual sections are depicted for a representative 3134 nucleus. As one focuses on 0.18 micrometer sections through the nucleus, a continuous fiber of intense light emission is detected over 5-7 sections, which corresponds to GFP-GR binding to the continuous BVP/MMTV-LTR/ras array.

Expression of GFP-GR in 3134 Cell

1) Materials.

a) Recombinant DNA

The LacSwitch™ inducible mammalian expression system (Stratagene catalog number 217450) is supplied with the phagemid DNAs: p3'SS for constitutive expression of the *E. coli* lac repressor and hygromycin resistance drug selectable marker; pOPI3 CAT for lac repressor regulated expression from the Rous sarcoma virus (RSV)-LTR promoter and neomycin resistance drug selectable marker; and pOPRSVI CAT for lac repressor regulated expression from the Rous sarcoma virus (RSV)-LTR promoter and neomycin resistance drug selectable marker.

Using standard recombinant DNA methodology, cDNA encoding GFP-GR fusion (either with the C656G mutation in the steroid binding domain of rat GR as present in the plasmid pCI-nGFP-C656G or wild type ligand binding domain of rat GR as present in the plasmid pCI-nGFP-rGR) is subcloned into the vector pOPRSVI CAT phagemid (Stratagene) at the NotI site. The cDNA should contain at its 5' end Kozak consensus sequence for efficient utilization of the translational initiation codon ATG, and at its 3' end the translational termination sequence followed by multiple translation termination sequences in all three reading frames. The vector provides RSV-LTR that has been engineered to be regulated by *E. coli* lac repressor so that in the mammalian cells with lac repressor, the strong RSV LTR promoter is inducible by the addition of 5 mM isopropyl-beta-D-thiogalactopyranoside (IPTG). The vector also provides an intron in the 5' untranslated region to ensure proper processing of the nascent transcript and maturation into productive mRNA. The vector also provides at the 3' untranslated region, herpes simplex thymidine kinase (TK) polyadenylation signal to ensure polyadenylation and message stability.

All DNAs used for introduction into mammalian cells are prepared from *E. coli* by alkali lysis procedure followed by isopycnic centrifugation by banding twice in cesium chloride/ethidium bromide gradient. Ethidium is removed by repeated extraction with isopentyl alcohol and cesium chloride by dialysis against large volumes of 10 mM Tris-HCl, pH 8/1 mM EDTA (TE). After dialysis, DNA is extracted twice in phenol chloroform solution and then with chloroform before precipitation with 0.2 M sodium acetate (pH 5.5) and 70% ethanol at −20 C. After collecting the precipitate by centrifugation, the DNA is washed with cold 70% ethanol, air dried, and then resuspended at a concentration of 1-2.5 mg/ml in TE.

b) Cell Line

The 3134 cell line contains a 9 kb repeat of the MMTV LTR fused to Ha-v-ras protooncogene in a BPV-based mammalian vector transformed into mouse carcinoma cell line C127.

Derivatives of 3134 cell lines containing pTET-nGFP-C656G and pOP-nGFP-C656G have been generated allowing GFP-GR expression upon tetracycline withdrawal from 5 ug/ml or upon induction with IPTG (about 1 mM) using standard procedures and as recommended by the manufacturer of these inducible systems. Acceptable levels of GFP-GR is reached in these derivative cells after overnight induction of the regulatable promoters.

2) Maintenance of 3134 Cells

The 3134 cells are maintained in complete DMEM media [Dulbecco's Modified Eagle Medium (DMEM; Gibco-BRL catalog number 11965-084) supplement with 2 mM L-glutamine (Gibco-BRL catalog number 25030-024), 50 ug/ml gentamicin reagent (Gibco-BRL catalog number 15750-011), and 10% fetal bovine serum (Gibco-BRL catalog number 26140-079) as monolayer in 162 $cm^2$ cell culture flasks (Costar catalog number 3150) at 37 C in 5% $CO_2$ humidified air incubator. Upon confluence, cells are washed with Dulbecco's phosphate buffered saline (D-PBS) without calcium or magnesium and then treated with 6 ml of 0.05% trypsin/0.53 mM EDTA for several minutes at RT (Gibco-BRL catalog number 25300-062). After cells round up, the side of the flask is tapped to dislodge cells from the flask surface. Repeated pipetting of the cells about three times results in a single cell suspension. One fifth of the cell suspension is transferred to a fresh 162 $cm^2$ flask containing 25 ml of the complete DMEM media. The freshly diluted cells are returned to the 37 C/5% CO2 incubator.

3) Introduction of DNA into 3134 Cells by Electroporation 3134 cells grown to about 90% confluence are harvested using the trypsin-EDTA and the activity of the trypsin quenched by placing the single cell suspension into at least equal volume of complete DMEM. Cells are counted in a hemacytometer and concentrated by centrifugation in bench top centrifuge (Sorvall RT6000D at 2,000 rpm for 5 minutes at 4 C) after placing in 50 ml sterile conical tube (Falcon 2070). Supernatant is aspirated and cells are washed again using complete DMEM. After the second wash, the resulting cell pellet is resuspended at a concentration of 20 million-cells per 200 ul in cold DNA and placed on ice. In 1.7 ml sterile microtube, appropriate DNA to be transfected, from 1-50 ug of about 8 kb plasmid DNA (typically 1-20 ug), is placed. 200 ul 3134 cells is added and mixed well. The mixture is transferred to disposable electro chamber cuvettes (Gibco-BRL catalog number 11601-010) on ice. Cuvettes are placed into electroporation chamber and electroporated (Gibco-BRL Cell-Porator catalog series 1600; settings: 250 volts, 800 or 1180 microFarads, low resistance). Recovery on ice is allowed for 5 minutes. Then, cells are removed from the cuvette and transferred to 50 ml conical tube with complete DMEM at RT. Cells are plated out on 150×25 mm tissue culture dish (Falcon 3025) in 30 ml of complete DMEM containing about one fourth the content of the electroporation cuvette. Plates are placed in 37 C/5% $CO_2$ incubator. Next day, media is changed to fresh media and selected with appropriate drug. Every two days media is changed and selection maintained with the appropriate drug.

4) Stable 3134 Cell Line Containing Lac Repressor

Electroporation of 1 ug, 5 ug, 10 ug, 30 ug, and 60 ug p3'SS DNA into 20 million 3134 cells in 200 ul cold DMEM is performed as described above. One day following electroporation, cells are selected with 450 ug/ml hygromycin B (Calbiochem catalog number 40005) for about 10 days during which hygromycin resistant colonies arise. The colonies are isolated by treating with trypsin impregnated sterile 3 mm cloning discs (PGC Scientifics catalog number 09-060) and transferred into 24 well tissue culture cluster dish (Costar 3524; each well 16 mm) containing 2 ml of complete DMEM with 450 ug/ml hygromycin B. The cells are allowed to grow in the dish in a 37 C/5% $CO_2$ incubator until at least 50% confluence. Media is replaced every couple of days.

Cells are trypsinized and transferred to 100×20 mm dish (Falcon 3003) containing 10 ml of complete DMEM with 450 ug/ml hygromycin B. Then, at about confluence, cell are trypsinized and transferred to 150×25 mm dish with 30 ml of complete DMEM with 450 ug/ml hygromycin. Near confluence, cells were trypsinized and aliquot replated into 100 mm dish while the remaining cells are frozen down in 10% DMSO with complete DMEM at −70 C. Cells grown on 100 mm dishes are harvested at confluence. Extracts are prepared and tested by Western blotting with rabbit anti-lac repressor polyclonal antibody (Stratagene catalog number 217449) and detected using goat anti-rabbit IgG horseradish peroxidase conjugated antibody (Bio-rad catalog number 170-6515) and enhanced chemiluminescent ECL western blotting detection reagents (Amersham catalog number RPN 2106). Cells expressing high amounts of the lac repressor are recloned and used for electroporating the pOPRSVI CAT plasmid containing GFP-C656G or GFP-rGR fusion cDNA.

5) Stable 3134 Cell Line Containing IPTG-Inducible GFP-GR or GFP-Fusion Protein Expression System.

3134 cells showing high levels of constitutive lac repressor expression without cytotoxic effects are used for electroporating pOPRSVI CAT plasmid containing the appropriate GFP-fusion protein cDNA. Following similar regiment as described above, the cells are selected with 450 ug/ml hygromycin B as well as 500 ug/ml geneticin (Gibco-BRL catalog number 11811-031). Following about ten days after selection, again drug resistant colonies are isolated, expanded, and characterized. Characterization is achieved by examining uninduced as well as 5 mM IPTG induced cells using Southern blot analysis of the genomic DNA, Western blot analysis using antibody directed against GFP and GR or other steroid receptor, characterize for localization of the GFP-fusion protein on the MMTV LTR-tandem array upon exposure to the appropriate ligand. Cells with appropriate desirable characteristics are subcloned and serve as reagents for diagnostic purposes.

Additional GFP-Steroid Fusion Proteins

The same technology is used to prepare GFP fusions for each member of the steroid/thyroid receptor family, including the estrogen receptor, progesterone receptor, androgen receptor, mineralocorticoid receptor, thyroid receptor, retinoic acid receptor (RAR), RXR receptor, vitamin D receptor, and TCCD (dioxin) receptor. Chimeric proteins for each of the receptors is be prepared using GFP fused either to the N-terminus or the C-terminus of the appropriate receptor. The chimeras are tested for functional transcriptional transactivation activity, and for binding to cognate response elements using cell lines described below.

GFP-ER: For example, the glucocorticoid receptor portion of pCI-nGL1-C656G DNA has been replaced with a human estrogen receptor. The GFP-ER was found to be functional in both transcriptional activation as well as proper subcellular localization. This further demonstrates the utility of the expression vector as well as the GFP-tagging approach.

Modification of the GFP Fluorescent Moiety

The success of GFP-GR fusion in detecting and characterizing in vivo gene targeting indicates that modification and enhancement of the GFP polypeptide can be of considerable usefulness. These modifications include:

1) Changes in the excitation wavelength to permit activation of selected GFP fusions;
2) Changes in the emission wavelength to permit observation of selected GFP fusions (GFP's will emit with different colors);
3) Enhancements to the efficiency of excitation and emission (GFP's will be "brighter");
4) Enhancements of GFP-chimeric proteins production by engineering the GFP sequence for more efficient expression:
   a) increasing the steady state level of GFP-chimeric protein mRNA levels through enhanced transcription, transcript processing, and RNA stability;
   b) increasing translational efficiency of the GFP-chimeric proteins by conservative substitutions of the protein coding regions and/or by introducing codons preferred for translation in humans cells;
   c) increasing stability of the GFP-chimeric proteins by identification of protein destabilizing sequences and selective elimination of such turnover signals;
5) Changes in GFP to define the minimal fluorescing polypeptide that could function in a fusion protein.

For example, in plasmids pCI-nGL2-C656G; pCI-nGL3-C656G; pCI-nGL4-C656G; pCI-nGL5-C656G; pCI-nGL7-C656G; pCI-nGL9-C656G; pCI-nGL10-C656G; pCI-nGL11-C656G, blue variants of GFP are used. Additionally, in these plasmids, humanized codons encoding the fusion protein were utilized.

Additional Cell Lines

Human and other mammalian cell lines can be prepared containing receptor binding sites (receptor response elements) in multimerized arrays for direct visualization of in vivo gene targeting.

1) For each receptor, these arrays can be created by gene amplification. The receptor response element is fused to the dihydrofolate reductase (dHFR) gene, transfected into human cells, and integrants selected by resistance to methotrexate. After selection of the initial cell lines, further selection is applied using sequentially higher levels of methotrexate. This results in amplification of the dHFR/receptor response element sequence, providing an array to which the receptor/GFP fusion binding can be observed (directly analogous to the 3134 cell line for GR). Further details are provided below.

2) An alternative approach is to multimerize the receptor response element by synthetic DNA synthesis, then introduce this amplified element directly into mammalian cells. This can provide a concentrated target for GFP-receptor localization.

Generating Cells Having Tandem Arrays

An approach that is being used to generate tandem arrays in a re-engineered promoter to obtain a functional transcription unit:

1) the MMTV LTR in the plasmid pLTRLuc is being mutated by site directed mutagenesis to introduce appropriate restriction enzyme cleavage sites at approximately positions:
+110 from start of transcription (HindIII)
−40 from start of transcription (SalI)
−217 from start of transcription (XhoI)
−1100 from start of transcription (XmaI)

2) the MMTV LTR in the plasmid pLTRLuc is being mutated by site directed mutagenesis to introduce appropriate restriction enzyme cleavage sites at approximately positions:
+110 from start of transcription (HindIII)
−80 from start of transcription (SalI)
−217 from start of transcription (XhoI)
−1100 from start of transcription (XmaI)

3) the DNA from (1) and (2) are being subcloned into two luciferase reporter gene vectors from Promega called pGL3-Basic (catalog number 88-1737) and pRL-CMV (catalog number 1068-2003) by using HindIII and XmaI digests of (1) and (2) and pGL3-Basic DNAs and inserting the mutated LTR fragments from (1) and (2) into the polylinker region of pGL3-Basic. In the case of pRL-CMV, this DNA is cleaved with PstI and BglII and the mutated LTR fragments from (1) and (2) inserted in place of the CMV Immediate Early Enhancer/Promoter regions in the pRL-CMV vector using a PstI/HindIII adapter on one end of the fragment. Also, before the insertion of the mutated LTR DNAs from (1) and (2), the SalI site present in the pGL3-Basic is eliminated by digesting this vector with SalI, filling-in the end with DNA polymerase, and subsequent resealing of the filled-in end before transforming bacteria.

4) oligonucleotides containing the glucocorticoid response elements (GRE: 5' AGAACAnnnTGTTCT 3') (SEQ ID NO:4) or estrogen response elements (ERE: 5' AGGTCAnnnTGACCT 3') (SEQ ID NO:5) are synthesized and then annealed (e.g., oligonucleotide 1 and 2; or oligonucleotide 3 and 4) such that one end contains a cohesive end for SalI and the other XhoI. Some examples of such oligonucleotides are (where the lower case letters are spacer bases and in the above designation would have been designated as "n"):

```
oligonucleotide 1: (SEQ ID NO:6):
5'tcgagcgcgcaAGAACAcagTGTTCTgacgacacgaAGAACAggaTGTTCTcgtacagtg 3' oligonucleotide 2: (SEQ ID NO:7):
5'tcgacactgtacgAGAACAtccTGTTCTtcgtgtcgtcAGAACActgTGTTCTtgcgcgc 3' oligonucleotide 3: (SEQ ID NO:8):
5'tcgagcgcgcaAGGTCAcagTGACCTgacgacacgaAGGTCAggaTGACCTcgtacagtg 3' oligonucleotide 4: (SEQ ID NO:9):
5'tcgacactgtacgAGGTCAtccTGACCTtcgtgtcgtcAGGTCActgTGACCTtgcgcgc 3'
```

5) the annealed oligonucleotides (1 and 2; or 3 and 4) are then ligated to generate large arrays in a perfect head-to-tail tandem array; these arrays may go through subcloning steps in bacteria to build larger arrays from smaller ones as well as to verify the integrity of the DNA sequence in the array by DNA sequencing.

6) the multimerized arrays from (5) are then inserted into the SalI/XhoI site in the mutated LTR of (3).

7) also, an additional series of constructs are also made lacking the region from
−217 to
−1100 of the LTR by restriction enzyme digestion with Xho I and MluI for the pGL3-Basic vector derived clones of (6), filling in the XhoI/MluI cohesive ends, and resealing the blunt ends to generate a multimerized tandem array of a DNA binding site driving the expression of the luciferase gene only through the binding sites in the array and the region of the LTR containing the signal for the start point of transcription (the TATA box and the initiator sequence).

8) stable mammalian cell lines (e.g., from human origin or Chinese hamster ovary (CHO)) are generated with the DNAs from (6) and (7) after linearization of the DNA, e.g. with BamHI and KpnI for the pGL3-Basic based DNAs and BamHI for the pRL-CMV based DNAs, and transfecting or electroporating these DNAs into cells, as is commonly done to introduce foreign DNA into cell. Also included in the transfection or electroporation is a DNA for a drug selectable marker such as neomycin gene or hygromycin that allows for drug selection (e.g., G418 or hygromycin, respectively) of cells that have taken up the foreign. DNA. In addition, green fluorescent protein (GFP)-tagged glucocorticoid, estrogen, and orphan receptors or DNA binding proteins appropriate for the factor DNA-binding DNA element is also co-transfected or electroporated.

9) isolated clones from drug selected cells from (8) are characterized for the number of copies and dispersal of the introduced DNAs from (6) and (7). Also, characterized is the amount of fluorescence derived from the GFP tagged-receptors or DNA-binding protein as well as the functionality of the expressed protein.

10) because most of the cell lines from (9) will have the foreign DNA integrated throughout the genome, localization of the GFP-tagged DNA binding molecule on the arrays in each of these transcription unit would result in intense fluorescence spot or focus. It is also possible that an extremely few number of cells will have integrated the foreign DNA in small arrays which should look like slight elongated intense spot. The desirable cells are those that contain visible intense foci due to binding of the GFP-tagged DNA binding protein on the transcription unit. In the case of the glucocorticoid receptor, the desirable cell lines are such that agonist dexamethasone treatment results in accumulation of the GFP-GR on the transcription unit to generate intense foci but not antagonist RU486 treatment.

11) DNAs from (6) or (7) will also be ligated to generate tandem arrays of each transcription unit and cloned into cosmid vector or phage P1 vector.

12) the tandem array transcription units will be treated as in (8).

13) the result of (11) will be characterized as in (9) and (10) to obtain cell lines with desirable properties.

14) DNA from (6) and (7) will be linked to a constitutively expressible dihydrofolate reductase (DHFR) gene by standard DNA subcloning techniques.

15) the DNA from (14) will be introduced into mammalian cells lacking the tumor suppressor gene, p53, using a similar procedure as in (8) except leaving out the drug selectable marker DNAs (due to the fact that DHFR gene is a drug selectable marker gene) and then selected for two weeks with methotrexate at a concentration about four times above the LD90. Selection media is replaced every 2-3 days. After methotrexate resistant colonies appear (in approximately two weeks), the colonies are pooled and part of the pool is frozen down while the remainder is used in a repeat selection with a concentration of methotrexate about four times higher than that previously used. This last selection procedure is repeated a number of times to finally select out cells with a highly amplified tandem array copies of DNAs containing the multimerized binding sites, the reporter gene, and the DHFR gene.

16) the cell lines after the last methotrexate selection are characterized for the presence of at least one tandem array and localization of the GFP-tagged DNA binding protein on this array analyzed. Localization on this array is manifested as a long linear highly fluorescent structure observed in the nucleus. In the case of GFP-GR, the localization on the array should occur upon treatment with agonist dexamethasone but not antagonist RU486.

17) other approaches to generating array envisioned is the use of site specific recombinases in vivo to generate precisely tailored tandem-arrays.

18) while items 1-16 focuses on the use of a genetically engineered artificial promoter/enhancer to generate arrays, tandem arrays may be made from just binding sites only or from natural regulatory DNAs harboring desirable factor-DNA binding sites.

19) since the higher eukaryotic genomes contain naturally occurring repetitive sequences, interactions of appropriately tagged DNA-binding protein with such naturally occurring sequences may also prove useful.

Using this general approach, functional receptor/cell line pairs can be established for each receptor-GFP fusion. These reagents provide a simple, rapid, straightforward, sensitive, and biologically relevant assay for each receptor.

Using standard recombinant DNA methodology, DNA encoding GFP-fusion protein sequences can be placed under the control of high expression eukaryotic promoter/enhancers (e.g. CMV promoter/enhancer, SV40 promoter/enhancer, RSV LTR, herpes simplex thymidine kinase [TK] promoter, etc.), naturally occurring inducible promoter/enhancers (e.g. metallothionine promoter/enhancer, MMTV LTR, heatshock promoter/enhancer, etc.), or synthetic inducible promoter/enhancers (e.g. GAL4-VP16 inducible system, Stratagene's LacSwitch™ inducible mammalian expression system (catalog number 217450), Life Technologies' Tet regulated expression system (catalog number 10583-011), etc.). These DNAs are introduced into mammalian cells along with DNA expressing a selectable marker (neomycin, hygromycin, zeocin, etc.) or screenable marker (e.g. fluorescence, foci formation, etc.) by standard protocol (e.g. calcium phosphate co-precipitation, electroporation, liposome-mediated transfection, viral infection, etc.). Following recovery of the cells to the introduction of DNA, approximately 1-3 days later, selectable agent is applied in the case of drug selectable marker to select for cells with stable integration of the selectable marker.

Upon continuous culturing of the cells under selection condition for an additional week during which clonal populations of cells will arise, the resulting cells are then characterized for the presence of the stably integrated DNA by Southern blot analysis and PCR analysis, for the expression of the GFP-fusion protein by Western blot analysis, flow cytometry, and microscopic examination, for participation in ligand-dependent translocation/transactivation by assaying the activity of reporter genes (e.g. chloramphenicol acetyltransferase, luciferase, beta-galactosidase, etc.) under the control of the appropriate ligand inducible promoter/enhancer (e.g., glucocorticoid response element containing promoter, estrogen response element containing promoter, etc.), and for localization on the target sequences in nuclei of expressing cells by high resolution fluorescence imaging systems (e.g. confocal laser scanning microscopy, cooled CCD camera microscopy, etc.). Alternatively, stable transformants expressing GFP-fusion proteins can be directly isolated by fluorescence activated cell sorting (FACS) using appropriate excitation wavelengths and emission detector.

Although less preferable at present, an alternative to isolating clones of stable transformants will be the isolation of pools of stable transformants. The use of cell line/expression system combination may necessitate such a generation of a pool of stable transformants.

Additionally, while it is presently most efficient to obtain stable cell lines, GFP-fusion expression plasmid can be transiently introduced into cells and analyzed for ligand-dependent translocation/nuclear targeting.

Use of Reagents

Because the use of GFP as a tag involves fusing a rather large protein (27 kDa) to GR, it was examined whether any GR activity has been compromised by GFP. To this end, GFP was fused to a rat GR with the C656G point mutation. This allowed selectively activation of GFP-GR without activating the endogenous receptor, and, thus, to assess the activity of the chimeric receptor independently of the endogenous GR. From the dose response curve and transcriptional activation of the MMTV LTR reporter gene (FIG. 3B), it is clear that GFP-GR can be selectively activated without activating the endogenous receptor.

By a number of criteria, GFP-GR functions very much like GR. In particular, the tagged receptor resides in the cytoplasm until activated by a ligand; it then translocates into the nucleus at a rate comparable to that previously reported (22). The rate and extent of GFP-GR translocation shows a dependence on the concentration of the activating ligand as well as a ligand specificity reflective of the native receptor. Furthermore, since both dexamethasone and RU486 treatment lead to complete translocation of GFP-GR from the cytoplasm to the nucleus in all cells, essentially all of the GFP-GR molecules exist in a conformation competent for both ligand binding and nuclear translocation. Once in the nucleus, GFP-GR's ability to activate the transcription of a MMTV LTR reporter gene depends on the type of activating ligand, consistent with previous results for GR. In the case of a potent agonist, dexamethasone, less GFP-GR is required for activation of transiently introduced MMTV LTRLuc reporter gene than for the endogenous GR, indicating that even with respect to transactivation potential, the presence of GFP has not altered the transcriptional potency ascribed to the C656G point mutation. Thus, in all aspects, the presence of GFP appears not to have affected normal GR function and has a general utility for studying the mechanisms of transcriptional regulation in vivo.

Since the S65T variant of GFP used here is highly excitable at 489 nm wavelength and resistant to photobleaching, it was possible to follow the course of cytoplasm-to-nuclear translocation of GR in a single living cell for an extended period of time. Upon binding to dexamethasone, GFP-GR moves vectorially toward the nucleus. Inhibition of import by chilling indicates that this transport is facilitated. Accumulation of GFP-GR along fibrillar structures before dexamethasone addition, and in the perinuclear region after dexamethasone addition, suggests that the cytoskeleton is involved in the transport process. Finally, the pulsatile brightness changes in the perinuclear region support an energy- and microtubule-dependent active transport process.

The rate of translocation of GFP-GR was dependent on hormone concentration, reflecting the dose- and time-dependence of GR action. This suggests that the rate of translocation contributes to GR function. The present invention indicates that cells having multiple copies of the response element in fluorescently detectable array can be a useful model to study reagents that modify rates of nuclear translocation and response element binding.

Finally, it is well-known that DNA in the nucleus is localized in a non-random fashion. The study of the pattern of nuclear fluorescence with GFP-GR supports the idea of an inherent order in the organization of the interphase nuclei and may reflect structures related to this organization. The reproducibility in the pattern of GFP-GR accumulation between neighboring nuclei reflects an inherent order of the interphase nucleus with regards to both GR-target site architecture (the foci of bright fluorescence) as well as transcriptionally incompetent GFP-GR, which appears to accumulate in a reticular pattern, reminiscent of association with the nuclear matrix. Thus, functional differences in GFP-GR due to hormone-specific effects (e.g., dexamethasone vs. RU486) are reflected in the patterns of GFP-GR intranuclear accumulation, indicating a general utility of understanding intranuclear localization of GR in addressing hormone-mediated actions.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A chimeric protein comprising a green fluorescent protein fused to a transcription factor, wherein the green fluorescent protein comprises a tripeptide sequence in the order threonine-tyrosine-glycine that is autocatalyzed to form a chromophore which can be excited by 488 or 489 nm laser light or its emission at 509 or 511 nm can be detected using a standard fluorescein filter set; or which can be excited at 480 nm light from a xenon short arc lamp (XBO) and analyzed for its emission around 535 nm, and wherein the green fluorescent protein functions as a fluorescent protein.

2. The chimeric protein of claim 1, wherein the green fluorescent protein is a *Aequorea* green fluorescent protein having the amino acid sequence of SEQ ID NO:2 beginning at methionine at amino acid position 23 and ending at lysine at amino acid position 260.

3. The chimeric protein of claim 1, wherein the green fluorescent protein is fused to the transcription factor via a peptide linker.

4. The chimeric protein of claim 3, wherein the peptide linker comprises five glycine-alanine repeating units.

5. The chimeric protein of claim 1, wherein the threonine-tyrosine-glycine sequence is located at residues 87 to 89 of SEQ ID NO:2.

6. The chimeric protein of claim 1, wherein the green fluorescent protein contains 238 amino acids.

7. A chimeric protein comprising a green fluorescent protein fused to a transcription factor, wherein the green fluorescent protein comprises a tripeptide sequence in the order Xa-tyrosine-glycine that undergoes an autocatalyzed reaction to form a chromophore, wherein in the tripeptide, Xa is substituted with another amino acid that allows greater excitation of the chromophore at a lower energy or longer wavelength than the *Aequorea* green fluorescent protein having a primary peak absorption wavelength of 395 nm and secondary peak absorption wavelength of 470 nm; and wherein the green fluorescent protein functions as a fluorescent protein.

8. The chimeric protein of claim 7, wherein in the tripeptide, the Xa is substituted with cysteine, leucine, valine or alanine.

* * * * *